US006242244B1

(12) United States Patent
Donohue et al.

(10) Patent No.: US 6,242,244 B1
(45) Date of Patent: **\*Jun. 5, 2001**

(54) MICROBIAL SYSTEM FOR FORMALDEHYDE SENSING AND REMEDIATION

(75) Inventors: Timothy Donohue, Middleton, WI (US); Robert Barber, State College, PA (US); Vernon Witthuhn, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/192,983

(22) Filed: Nov. 16, 1998

Related U.S. Application Data

(60) Continuation-in-part of application No. 08/919,953, filed on Aug. 29, 1997, now Pat. No. 5,837,481, which is a division of application No. 08/608,241, filed on Feb. 28, 1996, now Pat. No. 5,747,328.

(51) Int. Cl.[7] .............................. C12N 1/20; C12N 1/21
(52) U.S. Cl. .................... 435/262.5; 435/252.1; 435/252.3
(58) Field of Search .................. 435/252.1, 252.3, 435/262, 262.5

(56) References Cited

U.S. PATENT DOCUMENTS

| | | | |
|---|---|---|---|
| 4,535,061 | 8/1985 | Chakrabarty et al. | 435/252.4 |
| 4,593,003 | 6/1986 | Vandenbergh | 435/473 |
| 4,806,482 | 2/1989 | Horowitz | 435/262 |
| 4,833,086 | 5/1989 | Horowitz | 435/252.1 |
| 4,992,174 | 2/1991 | Caplan et al. | 210/610 |
| 5,079,166 | 1/1992 | Winter et al. | 435/262 |
| 5,196,339 | 3/1993 | Hanson et al. | 435/262 |
| 5,242,825 | 9/1993 | Mueller et al. | 435/253.3 |
| 5,283,192 | 2/1994 | Rusin | 435/252.31 |
| 5,352,608 | 10/1994 | Kaplan et al. | 435/262 |
| 5,364,787 | 11/1994 | Orser et al. | 435/252.33 |
| 5,369,029 | 11/1994 | Broker et al. | 435/262.5 |
| 5,422,268 | 6/1995 | Rusin | 435/262 |
| 5,834,300 * | 11/1998 | Donohue et al. | 435/262.5 |

OTHER PUBLICATIONS

Allen, L.N., et al., "Construction of Broad–Host–Range Cosmid Cloning Vectors: Identificatin of Genes Necessary for Growth of *Mrthylobacterium organophilum* on Methanol," *J. Bacteriol.*, 161:955–969 (1985).

Barber, R., et al., "Characterization of a Glutathione–Dependent Formaldehyde Dehydrogenase for *Rhodobacter sphaeriods*," Abstract K–66 and poster session presented at 9th General Meeting of American Society of Microbiologyi, Las Vegas, Nevaga (May 23–27, 1994).

Barber, R., et al., "Physiological role and transcriptional regulation of a glutathione–dependent formaldehyde dehydrogenase from *Rhodobacter sphaeroides*," Abstract and Poster Session presented at Coled Spring Harbor Symposium on Molecular genetics of Macteria and Phase, Madison, Wisconsin (Aug. 2–7, 1994).

Barber, R., et al., "Method oxydation in *Rhodoobacter sphaeroides*: Role and regulation of a glutathione–dependent formaldehyde dehydrogenase," Raper Symposium, Dept. of Bacteriology, U of WI (Aug. 1995).

Barber, R., et al., "Characterization of a Glutathione–Dependent Formaldehyde Dehydrogenase from *Rhodobacter sphaeriodes*," *J. Bacteriol.*, 178 (1996).

Baumgartner, J.W., et al. "Transmembrane Signalling by a Hybrid Protein: Communication from the Domain of Chemoreceptor Trg that Recognizes Sugar–Binding Proteins to the Kinase/Phosphatase Domain of Osmosensor EnvZ," *J. Bacteriol.*, 176:1157–1163 (1994).

Chang, C., et al., "Arabidopsis Ethylene–Response Gene ETR1: Similarity of Product to Two–component Regulators," *Science*, 262:539–544 (1993).

de Vries, G.E., et al., "Physiological Regulation of *Paracoccus denitrificans* Metjanol Dehydrogenase Synthesis and Activity," *J. Bacteriol.*, 170:3731–3737 (1988).

Donohue, T., Seminar given in Whitewater, WI (Dec. 1993).

Donohue, T., Seminar given in Georgia (Jan. 1994).

Donohue, T., Seminar given in Houston, TX (Apr. 1994).

Dryden, S.C., et al., "Localization and structural analysis of the ribosomal RNA operons of *Rhodobacter sphaeroides,*"_Nucleic Acids Res., 18:7267–7277 (1990).

Engeland, K., et al., "Mutation of Agr–115 of human class III alcohol dehydrogenase: A binding site required for formaldehyde dehydrogenase activity and fatty acid activation," *Proc. Natl. Acad. Sci. USA*, 90:2491–2494 (1993).

Estonius, M., et al., "Residues Specific for Class III Alcohol Dehydrogenase. Site–Directed Mutagenesis of the Human Enzyme, " *Biochemistry*, 33:15080–15085 (1994).

Green. D.W., et al., "Inversion of the Substrate Specificity of Yeast Alcohol Dehydrogenase," *J. Biol. Chem.*, 268:7792–7798 (1993).

Harms, N., et al., "Identification of a two–compopnent regulatory system controlling methanol dehydrogenase synthesis in *Paracoccus denitrificans,*" *Mol. Microb.*, 8:457–470 (1993).

(List continued on next page.)

Primary Examiner—Robert A. Schwartzman
(74) Attorney, Agent, or Firm—Quarles & Brady LLP

(57) ABSTRACT

Environmental formaldehyde can be detected and remediated in a biological system that incorporates a bacterial cell containing suitable genetic sequences encoding a formaldehyde-inducible regulatory system. The system includes a transcriptional promoter that can be specifically induced in the presence of formaldehyde to transcribe an operably linked gene.

14 Claims, 3 Drawing Sheets

OTHER PUBLICATIONS

Jornvall, H., et al., "Characteristics of alcohol/polyol dehydrogenases: The zinc–containing long–chain alcohol dehydrogenases," *Eur. J. Biochem.*, 167:195–201 (1987).

Koivusalo, M., et al., "Glutathione–Dependent Formaldehyde Dehydrogenase (EC 1.2.1.1): Evidence for the Identity with Class III Alcohol Dehydrogenase," *Enzymology and Molecular Biology of Carbonyl Metabolism 3*, ed. H. Weiner et al., Plenum Press, NY (1990).

Koivusalo, M., et al., "Glutathione–Dependent Formaldehyde Dehydrogenase/Class III Alcohol Dehydrogenase: Further Characterization of the Rat Live Enzyme," *Enzymology and Molecular Biology of Carbonyl Metabolism 4*, ed. H. Weiner et al., Plenum Press, NY (1993).

Ota, I.M., et al., "A Yeast Protein Similar to Bacterial Two–Componebt Regulators," *Science*, 262:566–569 (1993).

Rott, M.A., et al., "Genetic Evidence for the Role of Isocytochrone $c_2$ in Photosynthetic Growth of *Rhodobacter sphaeroides* Spd Mutants," *J. Bactreriol.*, 175:358–366 (1993).

Sasnauskas, K., et al., "Cloning and analysis of a *Candida maltosa* gene which confers resistance to formaldehyde in *Saccharomyces cerevisiae*," Gene, 122:207–211 (1992).

Slooff, W., et al., "Exploratory Report Formaldehyde," National Institute of Public Health and Environmental Protection, The Netherlands (1992).

U.S. Environmental Protection Agency, "Health and Environmental Effects Profile for Formaldehyde" (1985).

Witthuhn, V.C., et al., "Identification of a two–component respone regulator that controls transcription of the adhI–cycI operon in *Thodobacter sphaeroids*," Abstract and Poster Session presented at Cold Spring Harbor Symposium on M olecular Genetics of Bacteria and Phage, Madison, WI (Aug. 2–7, 1994).

Azachi et al., Transformation of Formaldehyde by a Halomonas sp., *Can. J. Microbiol.* 41:548:553 (1995).

* cited by examiner

MICROBIAL SYSTEM FOR FORMALDEHYDE SENSING AND REMEDIATION

CROSS-REFERENCE TO RELATED APPLICATIONS

This application is a continuation-in-part of U.S. patent application Ser. No. 08/919,953, filed Aug. 29, 1997, which will issue as U.S. Pat. No. 5,837,481 on Nov. 17, 1998, which is a divisional application of U.S. patent application Ser. No. 08/608,241, filed Feb. 28, 1996, now U.S. Pat. No. 5,747,328, each of which are incorporated herein by reference in its entirety.

STATEMENT REGARDING FEDERALLY SPONSORED RESEARCH OR DEVELOPMENT

This invention made with United States Government support awarded by USDA, USDA Project Numbers 37262-5588 and 37306-0336; Hatch Project Number 3766. The United States Government has certain rights in this invention.

BACKGROUND OF THE INVENTION

Increasing concern over environmental contaminants has made desirable systems for detecting and remediating such contaminants. Among the more important contaminants of industrial societies is formaldehyde. The health and environmental effects of formaldehyde have been well characterized, as has their distribution in soil and water. See, e.g. "Health and Environmental Effects Profile for Formaldehyde," Report No. EPA/600/X-85/362, Environmental Criteria and Assessment Office, Office of Health and Environmental Assessment, Office of Research and Development, US Environmental Protection Agency, Cincinnati, Ohio 45268 (NTIS document number PB88-174958) (October 1985) and "Exploratory Report Formaldehyde," Report No. 710401018, National Institute of Public Health and Environmental Protection, Bilthoven, The Netherlands (NTIS Report No. PB93-224483) (October 1992).

Evidence of formaldehyde carcinogenicity in rats and other epidemiological evidence have led to the classification of this compound as a probable human carcinogen. Formaldehyde is a common product of several industries (wood processing, paper production) that feed run-offs into aquatic ecosystems. Formaldehyde, which is present in approximately 2,000 entries of the Product Register Data Base, is also released from common cleaning agents, soaps, shampoos, paints, and lacquers. Little is known about how cells sense this toxin, metabolize it, or control the genes that are required for formaldehyde oxidation.

Existing chemical monitors for formaldehyde are time-consuming, exhibit variable sensitivity, and are prone to cross-reactivity with other aldehydes. It would be useful to utilize a biological system capable of specific response to, and detection of, formaldehyde. Moreover, a system capable of responding to the presence of formaldehyde could be useful as a bioremediation tool to reduce or eliminate formaldehyde as an environmental contaminant. However, to date, no biological formaldehyde-inducible detection or remediation system has been constructed.

Most organisms have the ability, using various metabolic pathways, to generate both energy and carbon skeletons by oxidizing a wide spectrum of substrates, including substrates that are themselves environmental toxins. Formaldehyde oxidation can be mediated by Class III alcohol dehydrogenase enzymes, also called glutathione-dependent formaldehyde-dehydrogenases or GSH-FDH, which are a well-studied class of the zinc-dependent alcohol dehydrogenase protein family that is known in both prokaryotes and eukaryotes.

GSH-FDH enzymes are believed to perform different functions depending upon the cell type. In some organisms, GSH-FDH serves a role in the catabolism of methylated compounds. For example, some methylotrophic microbes use GSH-FDH to generate carbon skeletons and NADH from the formaldehyde that is produced from methanol oxidation. In non-methylotrophic organisms, GSH-FDH rids the cells of toxic formaldehyde produced from the oxidation of methylated substrates such as choline, sarcosine, methionine, O-methylated amino acids, methanol, methyl halides, or several N-, O-, or S-methylated xenobiotics. In both roles, GSH-FDH enzymes generate reducing power, NADH, and a product, S-formylglutathione, that can be subsequently oxidized to generate one-carbon compounds such as formate or carbon dioxide.

In particular, S-hydroxy methyl glutathione (HMGSH), an adduct formed spontaneously by glutathione (GSH) and formaldehyde (HCHO) (reaction 1), is both the preferred in vitro substrate and the presumed physiologically relevant substrate in vivo for GSH-FDH enzymes (reaction 2).

(1) HCHO+GSH→HMGSH (spontaneous)

(2) HMGSH+AND$^+$→S-formylglutathione+NADH+H$^+$

Unlike other classes of alcohol dehydrogenase enzymes, members of the GSH-FDH family do not exhibit appreciable activity with short aliphatic alcohol substrates such as ethanol. Instead, GSH-FDH enzymes catalyze the AND-dependent oxidation of long chain hydroxylated fatty acids (i.e., 12-hydroxydodecanoic acid) or long chain alcohols.

In the photosynthetic purple bacterium *Rhodobacter sphaeroides*, a glutathione-dependent formaldehyde dehydrogenase protein (AdhI) is encoded by adhI in an operon that also includes cycI which encodes an isoform of the cytochrome c$_2$ family of electron transport proteins. The AdhI protein encoded by adhI has the characteristic substrate preference of a glutathione-dependent formaldehyde dehydrogenase. Ferguson plot analysis, using zymograms, suggests that the functional form of AdhI is a homodimer of approximately 40 kDa subunits, analogous to other such enzymes. The complete nucleotide sequence of *R. sphaeroides* adhI has not heretofore been disclosed.

Expression of the adhI-cycI operon is thought to be regulated since the abundance of isocytochrome c$_2$ was increased by a trans-acting regulatory mutation. Rott, et al., "Genetic Evidence for the Role of Isocytochrome c$_2$ in Photosynthetic Growth of *Rhodobacter sphaeroides* Spd Mutants," *J. Bacteriol.* 175:358–66 (1993).

BRIEF SUMMARY OF THE INVENTION

The present invention is summarized in that a protein-encoding genetic sequence that is operably linked to a formaldehyde-inducible transcriptional promoter sequence and a cis-acting operator in a genetic construct can be specifically transcribed in a bacterial host cell that contains a formaldehyde-specific regulatory system disclosed herein, when the cell is exposed to formaldehyde. The genetic construct is useful in an assay for detecting formaldehyde.

The invention is further summarized in that a formaldehyde dehydrogenase gene that is operably linked to the formaldehyde-inducible transcriptional promoter/operator sequence in a genetic construct can be specifically transcribed in a bacterial host cell that contains the formaldehyde-specific regulatory system when the cell is exposed to formaldehyde, thereby producing a formaldehyde dehydrogenase enzyme. The construct is useful in a bioremediation assay capable of metabolizing formaldehyde into single-carbon skeletons.

The invention is further summarized in that a bacterial cell can respond in a biosensing assay or bioremediation assay if it contains a genetic construct that includes a protein-encoding genetic sequence operably linked to the formaldehyde-inducible transcriptional promoter sequence linked to a cis-acting operator, a trans-acting regulator of the transcriptional promoter and a formaldehyde-specific sensor.

When linked to the cis-acting operator sequence described herein, the transcriptional promoter can be induced in the presence of formaldehyde to transcribe the operably linked protein-encoding sequence in the presence of a two-component regulatory system (also referred to as a histidine kinase-response regulator) wherein one or more components sense the presence of formaldehyde (hereinafter referred to as a "sensor") and another component, the so-called "response regulator") regulates transcription of the protein-encoding sequence. The sensor and the regulator molecule can be provided as proteins or can be encoded on a genetic construct when placed under the control of a suitable promoter. The gene or genes encoding the sensor and/or regulator can be provided on the same construct as the formaldehyde-inducible promoter operably linked to the coding sequence, or can be provided on separate constructs. If provided on the same construct, the gene or genes should be under the transcriptional control of an unregulated or constitutive promoter.

The present invention is also summarized in that a method for detecting the presence of formaldehyde includes the steps of (1) adding to a sample to be tested a bacterial cell that contains (a) a genetic construct that includes a genetic sequence encoding a detectable protein operably linked to the disclosed promoter/operator sequence, and further contains (b) a trans-acting regulator of the formaldehyde-specific transcriptional promoter as well as (c) a formaldehyde-specific sensor, and then (2) monitoring for the presence of the detectable protein.

The present invention is also summarized in that a method for remediating formaldehyde from an environment includes the steps of (1) adding to a formaldehyde-containing sample a bacterial cell that contains (a) a genetic construct that includes a formaldehyde dehydrogenase gene operably linked to the promoter/operator sequence disclosed herein, and further contains (b) a trans-acting regulator of the transcriptional promoter and (c) a formaldehyde-specific sensor, and then (2) monitoring a decrease in formaldehyde level in the environment.

DETAILED DESCRIPTION OF THE INVENTION

In its broadest sense, the present invention is a system for regulating transcription of a polynucleotide in a bacterial host cell that can be induced when the cell is exposed to formaldehyde. The transcriptional regulation scheme contemplated herein is a regulatory system of the type reviewed by Bourret, R. B. et al., *Annual Rev.; Biochem*; 60:401–411 (1991), incorporated herein by reference, and by Parkinson, J. S. and E. C. Kofoid, *Annual Rev. Genetics*, 26:71–112 (1992), incorporated herein by reference.

In brief, a histidine kinase-response regulatory system includes a sensor that specifically detects a target molecule and, upon detection, transmits a signal to a trans-acting effector or regulatory protein that modulates activity elsewhere in a cell. Modulation can be at the transcriptional, translational, or functional level. In structurally similar systems, the signal is generally transmitted by autophosphorylation of the sensor followed by transphosphorylation by the sensor of the regulator. In the present system, the regulator is a DNA-binding repressor protein. Reference herein to the repressor protein, the effector protein or regulatory protein are all intended to refer to this molecule.

Incorporated U.S. Pat. No. 5,747,328, from which this application claims priority, disclosed that a single polynucleotide fragment (genomic clone pUI8017) contributed all necessary repressor and sensor functions of the formaldehyde-inducible regulatory system and it was predicted on the basis of preliminary sequence data that the regulatory system contained thereon encoded no secondary sensor protein. Because the fragment competently contributed the necessary functions, it was further predicted that any additional system component would likely be encoded on the same polynucleotide clone. The competent DNA fragment is obtained from a genomic cosmid library of wild-type *Rhodobacter sphaeroides* (strain 2.4.1) DNA. The genomic library was described by Dryden, S. and S. Kaplan, "Localization and Structural analysis of the ribosomal RNA operons of *Rhodobacter sphaeroides*," N. A. R. 18:7267 (1990), incorporated herein by reference. The genomic clone pUI8017 was prepared in cosmid vector pLA2917, which was itself described by Allen, L. N. and R. S. Hanson, "Construction of Broad-Host-Range Cosmid Cloning Vectors: Identification of Genes Necessary for Growth of *Methylobacterium organophilum* on Methanol," J. Bact. 161:955 (1985), incorporated herein by reference.

Figure 2:
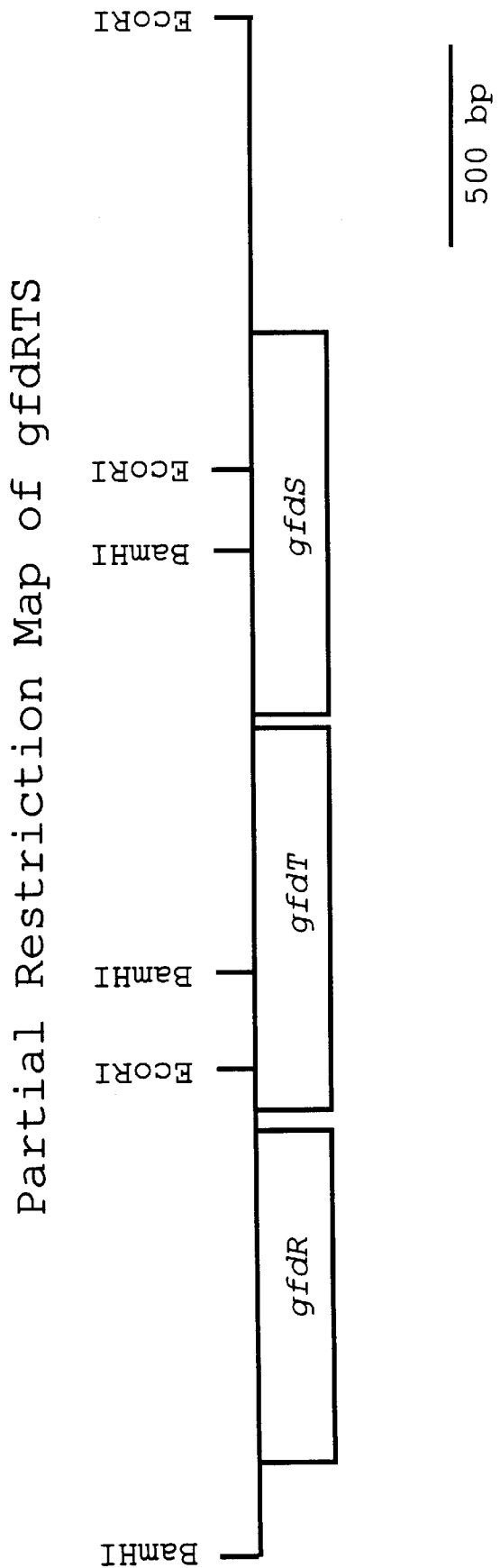
FIG. 2 shows a partial restriction map of genomic clone pUI8017 that contains a polynucleotide having at least three open reading frames that encode a repressor (formerly SpdR, now GfdR), a polynucleotide that encodes a transmembrane sensor protein (GfdT) and a polynucleotide that encodes a soluble sensor protein (formerly SpdS, now GfdS).

In nature, the sequences encoding the sensor and the repressor of the present invention are linked members of a single operon. FIG. 2 shows a partial restriction map of genomic clone pUI8017 that contains the sequences that encodes the repressor (formerly SpdR, now GfdR), and a pair of sensor components which include a transmembrane component (GfdT), and a soluble component (formerly SpdS, now GfdS). This portion of a bacterial genome can be obtained from other organisms by using a genetic probe corresponding to the exemplified sequence or any portion thereof. Since organisms may contain genes related to the gfdr, gfdT and gfds genes, the hybridization conditions employed should be sufficiently stringent to detect only the desired gene regions.

A preferred repressor protein has the amino acid sequence shown in SEQ ID NO:4, which shows significant homology to response regulators of histidine kinase response regulator systems. A suitable and preferred DNA fragment that encodes the full length coding sequence of such a repressor is shown at bases 215–895 of SEQ ID NO:3. The sequence possesses all of the most highly conserved residues and many of the lesser-conserved residues of the N-terminal consensus sequence proposed by Volz, Biochemistry 32: 11741 (1993). The deduced amino acid sequence also possesses a C-terminal LuxR family helix-turn-helix DNA binding motif, shown between amino acids 175 and 202 of SEQ ID NO:4. By analogizing with other members of this family, it is believed that the site of phosphorylation is the aspartate residue at amino acid 62 of the protein shown in SEQ ID NO:4. The DNA binding motif and the structural relationship to the response-regulating portions of other regulatory systems suggest that this protein binds at or near the formaldehyde-specific promoter, and negatively regulates transcription from the promoter, as was noted above.

Of course it is understood from consideration of this specification, that the entire repressor protein molecule or gene may not be required for formaldehyde-specific regulation. As will become apparent, the only required amino acids of the regulator protein (or the corresponding nucleic acid sequences in a genetic construct encoding such a protein) are the portions of the protein used for DNA binding at or near the promoter region and the portions used for receiving a phosphorylation signal from a formaldehyde-specific sensor. All modifications, alterations, or deletions of the repressor that do not otherwise interfere with the ability of the molecule to function as described are intended to fall within the scope of the present invention.

The DNA-binding repressor protein can be provided in a host cell by a genetic construct comprising a polynucleotide sequence that encodes a polypeptide capable of repressing transcription from the formaldehyde specific promoter where the polynucleotide sequence is under the control of a promoter functional in the host cell.

The next aspect of the invention is the ability to sense the presence of environmental formaldehyde in a sample and to direct a signal to the repressor protein in response thereto. In one embodiment of the system disclosed herein, formaldehyde recognition is provided by a sensor (which has at least one component and may have two components) that interacts with or "senses" formaldehyde and then interacts with the regulator component of the regulatory system.

The "sensor" of the preferred embodiment apparently comprises at least two proteins, rather than the single protein predicted in U.S. Pat. No. 5,474,328. An open reading frame (ORF) at bases 993–2165 of SEQ ID NO:3 encodes the deduced amino acid sequence of SEQ ID NO:5. Hydropathy analysis of the deduced amino acid sequence reveals that the ORF encodes a polypeptide having properties characteristic of a transmembrane protein, and has been designated gfdT. In addition to the transmembrane protein, the sequence between bases 2236–4437 of SEQ ID NO:3 also encodes a deduced amino acid sequence as shown in SEQ ID NO:6. This second ORF, designated gfds, encodes an amino acid sequence thought to be that of a soluble protein.

While both the transmembrane protein and the soluble protein may be important components of the system, the spatial interaction between the proteins is not yet known, nor is it known whether both components are strictly required. By analogy to other systems, it is thought that a histidine residue near the carboxy terminal end of the soluble sensor protein GfdS (amino acid 367 of SEQ ID NO:6) may be dephosphorylated when formaldehyde binds to the transmembrane receptor protein GfdT. In the absence of formaldehyde, the phosphate on GfdS may be transferred to an aspartate residue of the repressor (GfdR) described elsewhere herein. Because the non-phosphorylated repressor has reduced ability to bind to the promoter/operator region, its attachment to the DNA is reduced, facilitating transcription of the operably-linked gene. Without being limited as to theory, formaldehyde present in the extracellular environment may signal its presence by becoming bound to, or otherwise associated with, the transmembrane receptor, such that a conformational change in the transmembrane protein transduces the signal to the soluble sensor protein. In the absence of formaldehyde, the soluble sensor histidine kinase, in turn, may no longer phosphorylate the regulator, thereby increasing the ability of the regulator to bind to the operator and repressing transcription from the promoter. It is understood that the invention in its broadest forms is not intended to be limited to the transcription and subsequent translation of any particular indicator gene operably linked to the formaldehyde-inducible promoter that is regulated in the regulatory system.

Moreover, strictly speaking, formaldehyde itself may not be the effector molecule that induces the regulatory system. Rather, it is likely that a adduct of formaldehyde may actually be the target molecule of the system described herein. A likely adduct is S-hydroxy methyl glutathione (HMGSH), which is formed non-enzymatically in the aqueous environment of cells or in nature. It is abundantly clear that the system is responsive to the presence of formaldehyde and for purposes of this application, convenient reference is made to induction "by formaldehyde," with the understanding that subsequent studies may reveal that the true effector molecule is not formaldehyde but rather a related molecule or adduct.

The formaldehyde that induces the expression system can derive from any source, including industrial or commercial waste, or a biological or chemical degradation product of such waste. For example, the system can respond to a methyl donor (such as choline, sarcosine, methionine, O-methylated amino acids, methanol, methyl halides, or several N-, O-, or S-methylated xenobiotics) if the bacterial host cell has the facility to convert the methyl donor into formaldehyde or if another conversion mechanism is provided.

In the present system, when the repressor is bound to the promoter region there is virtually no transcription of the operably attached gene in the absence of formaldehyde. For purposes of this invention, "virtually no transcription" means less than 10% and preferably less than 1% of the transcription observed in the induced, or de-repressed, state. For purposes of this patent application, "induction" means an increase in transcription from the formaldehyde-inducible promoter of more than 10-fold from its uninduced state and preferably an increase of greater than 100-fold. Transcriptional increases as high as about 1000-fold are contemplated.

The system is responsive to formaldehyde even at very low levels. Micromolar or higher quantities of formaldehyde are sufficient in aqueous environments to induce the expression system of the present invention. Comparable levels are likely sufficient in other environments as well. At a lower limit, the system can be induced in the presence of less than 100 micromolar and more preferably less than 10 micromolar formaldehyde in *R. sphaeroides*. The lower induction limit is thought to be less than 1 micromolar (1 ppm), say 0.01 micromolar. In other organisms, the induction level may vary, depending upon the threshold level of toxicity of formaldehyde to the organism. It is, of course, understood that the upper and lower induction limits and the window of effectiveness are readily determined in any organism using standard analytical methods.

The invention finds particular utility as a biosensor system by which the presence of formaldehyde in an environment is revealed by the regulated production of a detectable protein. If the invention is used for formaldehyde detection, a suitable bacterial strain is added to an environmental sample to be analyzed, and the sample is monitored for changes in an indicator gene, as is described in more detail below.

Alternatively, formaldehyde can be converted into other substances to promote a remediating effect upon the environment when the indicator gene is replaced by a gene A that can oxidize formaldehyde. In such a method, it would be possible to observe a decrease in formaldehyde level in the environment.

For purposes of this application, a "sample" can be an aliquot suitable for laboratory analysis, but can equally well be a larger-scale location for which remediation is desired, such as a body of water which can include, but is not limited to, a water treatment facility, a lake, a pond, a river or a stream.

In a related method, the ability to respond to the presence of formaldehyde can also be used to effect production of a desired protein for reasons other than formaldehyde detection or remediation. For example, it may be desirable to induce one or more cellular pathways to degrade other agents commonly found in formaldehyde-containing environments. In such a method, it is also envisioned that a cascade of such responses could be carried out in a single bacterial cell type.

The methods may be practiced by providing the bacterial cells on an immobilized surface or substrate or the cells can be unattached.

In addition to the above-noted methods, the present invention also provides a genetic construct for use in the methods. By providing a genetic construct, transfer of the disclosed system into other organisms is facilitated. The exemplified embodiment of the system described herein is operative in wild type *Rhodobacter sphaeroides*, a purple, non-sulfur photosynthetic bacterium typically found in low oxygen aquatic environments and in mutants thereof that retain the relevant genes as described herein. Moreover, using genetic materials of the type disclosed herein, it is readily possible to transfer the genetic components of this system into bacterial host cells including facultative or strict anaerobes and aerobes that populate, for example, soil, air, high acid (acidophiles), or high salt (halophiles) environments and the like, and into bacterial strains that selectively populate hot and cold temperature environments. Bergey's Manual of Determinative Bacteriology, 9th ed., Williams & Wilkins, Baltimore, Md., John G. Holt, ed. (1994), incorporated herein by reference, is an authoritative index of known bacteria that includes lists of various organisms meeting these criteria. Thus, in addition to using *Rhodobacter sphaeroides* in a remediation or detection assay, other bacterial cells containing non-native constructs of the type described herein are also within the scope of the present invention.

A suitable genetic construct includes an indicator or effector gene under the control of the formaldehyde-inducible promoter, which can be a gene suitable for detection or remediation of formaldehyde or any other gene whose product can be detected. If a self-replicating construct is used, the construct also includes those additional elements, such as an origin of replication and a selectable marker, which are necessary for replication and maintenance in a bacterial host. Alternative constructs could be incorporated directly into the chromosomal material of the host organism. Other genes may also be provided on the construct without interfering with the present invention. The construct can be, for example, a plasmid, cosmid or phagemid.

It is understood that the formaldehyde-inducibility depends upon both the promoter and the operably linked cis-acting operator element near the promoter (preferably provided within 50 nucleotides, more preferably within 25 nucleotides, of the promoter sequence). The operator is thought to be the binding site of the regulatory protein described elsewhere herein and is also believed to be the inverted repeat sequence identified elsewhere herein. The operator, which is encoded on the same exemplified genetic fragment as the promoter, is physically separable from the promoter and has separate utility as a genetic element that may be placed near any other promoter to confer formaldehyde-inducibility upon that other promoter. This may be desirable in a particular expression system where formaldehyde inducibility is desired but where a stronger (or weaker) promoter than the one that naturally promotes transcription of the *R. sphaeroides* adhI-cycI operon is also desired. It may also be useful for transfer to other organisms where other promoters are preferred.

For purposes of convenience in this application, all references to the formaldehyde-inducible promoter, or to the "promoter/operator" are intended to include reference to the cis-acting operator sequence, with the understanding that the two elements, while physically linked, are separable and contribute separate functionality to the system described herein. Reference herein to the promoter and operator working together to direct transcription are intended to mean that transcription from the promoter occurs only when the regulatory protein is not bound to the nearby operator sequence, and moreover that when the regulatory protein is bound to the operator, virtually no transcription from the promoter can take place.

Figure 1A:
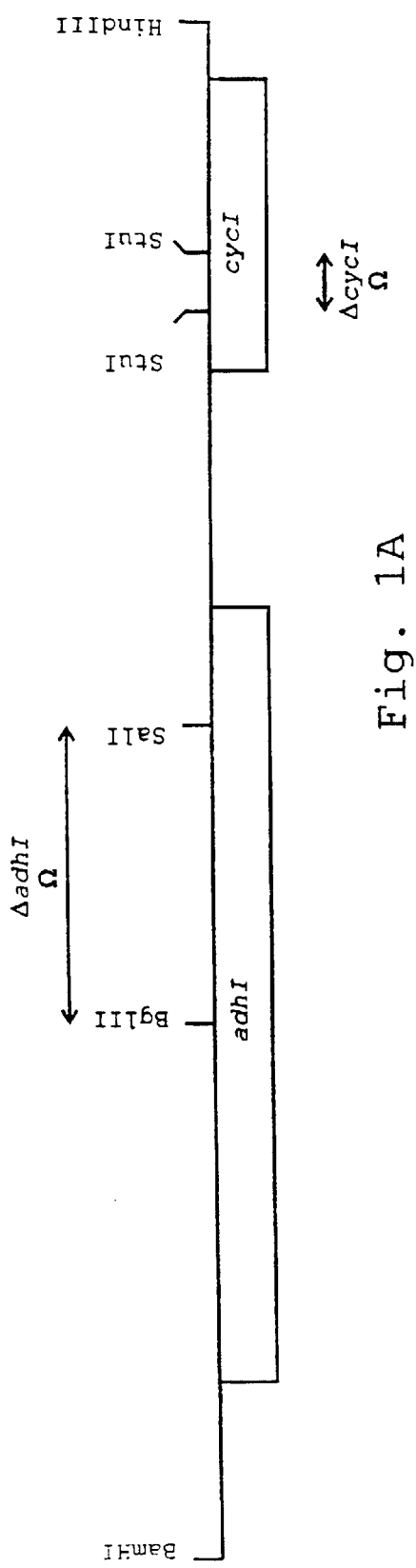
FIG. 1a shows a partial restriction map of a portion of the *R. sphaeroides* genome that encodes the adhI-cycI operon.
Figure 1B:
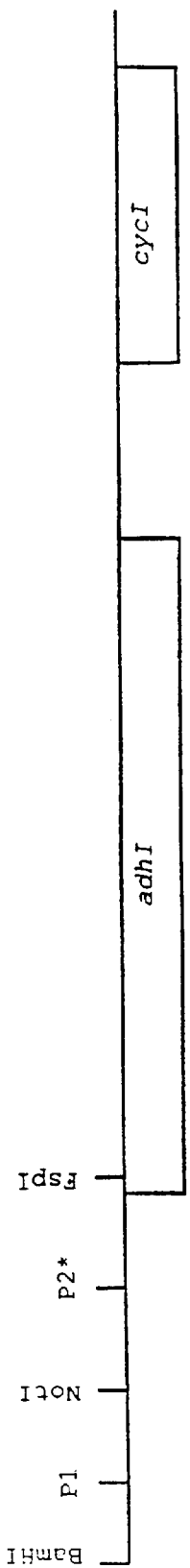
FIG. 1b shows a partial restriction map of the promoter portion of the adhI-cycI operon.

A suitable formaldehyde-inducible promoter region that can be isolated from the upstream portion of an operon from the *Rhodobacter sphaeroides* genome that encodes adhI-cycI, is shown as bases numbered 1–345 of SEQ. ID. NO:1. The portion of the *R. sphaeroides* genome that contains the adhI-cycI operon is shown schematically in the partial restriction map of FIG. 1*a*. The promoter portion of the operon is highlighted in FIG. 1*b*. In vivo, two transcription products covering the adhI-cycI operon are observed, and, indeed, two genetic segments recognized as having promoter activity are present in that portion of SEQ ID NO:1. Relative to the adhI translational start site (base number 346 of SEQ ID NO:1), the two in vivo transcripts map to positions −267 and −49, which correspond in SEQ ID NO:1 to base numbers 79 and 297, respectively. SEQ ID NO:2 depicts the full-length amino acid sequence of AdhI.

Although both promoters may be present in a genetic construct within the scope of the present invention, only the promoter responsible for the −49 transcript is sensitive to the regulatory network described herein and to the controlling metabolic signals.

The formaldehyde-inducible promoter/operator is under the proximate control of a DNA-binding protein that binds to, and negatively regulates, the promoter described above, when formaldehyde is absent from the environment. Although the specific nucleotides of the operator that reversibly interact with the repressor protein have not been determined with specificity, an inverted repeat sequence between the −10 sequence and the translation start sequence is thought to be the binding site of the repressor. The inverted repeat portion is shown between bases 289 and 310.

It is not scientifically possible to rule out the possibility that an additional set of induction proteins may also be involved in induction of this expression system. Therefore, total induction in the system may be higher if additional activating proteins are available. In any event, significant induction is observed in the system as described.

In view of the preceding analysis of the promoter region, the following portions of SEQ ID NO:1 are suitable promoter sequences, listed in order of increasing preference: bases 1 to 345, bases 85 to 345, bases 109 to 345, bases 128 to 345, bases 157 to 345, bases 173 to 345, bases 196 to 345, bases 220 to 345, and bases 241 to 345. An even smaller portion that comprises the −10 and −35 regions and the inverted repeat may also function adequately. It is probable that the promoter function resides entirely in the region between bases 1 and 310, and thus, yet more preferred promoter regions are those identified above in this paragraph, except having a 3' end at base 310 rather than at base 345.

It will be appreciated by one of ordinary skill in the art upon consideration of this specification that only certain nucleotides of the promoter region are involved in the interaction with the formaldehyde-inducible regulatory system described herein and that, as long as the general requirements of all bacterial transcriptional promoters such as −35 and −10 sequences (ATGCCG and ATAGGT, respectively, in the exemplified embodiment) are provided, other portions of the promoter region may be altered, modified or deleted without departing from the spirit of the present invention, as long as the ability to modulate transcription in response to formaldehyde is maintained. Promoter activity can also be modified, for example, by altering the −35 and −10 sequences so that they have greater similarity to known consensus sequences.

The promoter can actively promote transcription without additional contribution of transcription-enhancing activator sequences, although these may be provided in a suitable construct. Other sequences that contribute to transcription are sometimes found in the 5' untranslated region upstream from a coding region. Thus, the inventors cannot rule out the possibility that other sequences upstream from the coding sequence shown in FIG. 1 may contribute to regulation of this promoter.

Likewise, it is also to be appreciated that genetic manipulation techniques may be applied to the promoter region to alter, particularly to strengthen, repressor binding. The binding of the repressor to the site can be altered by substituting bases in the binding site, thought to be the inverted repeat. It is also specifically envisioned that coordinate changes to both the promoter and its repressor can be made without departing from the spirit of the invention. By so modifying the promoter, an environment is created wherein a very tightly bound repressor protein further reduces the level of baseline transcription while the modified −35 and −10 sequences bring about higher transcription levels when the repressor is removed. The net effect will be an improved signal-to-noise ratio which will facilitate the detection of even smaller amounts of the target molecule.

It is unknown whether there is a preferred spatial or distance relationship between the inducible promoter and gene positioned downstream from the promoter, although the natural spatial relationship is considered to be preferred.

A vast number of genes can be linked to the inducible promoter. The selection of a gene for linkage is entirely dependent upon the desired response to the presence of formaldehyde, which may relate to detection or remediation of formaldehyde or may effect an entirely different activity. Generally speaking, a suitable gene is a gene that encodes a detectable protein, referred to herein as an "indicator gene." For purposes of this patent application, the term "indicator" or "indicator gene" is intended to include all bacterial detection systems, without regard to whether the molecule detected is a product of the indicator gene itself or is a substrate for the gene product. The art is replete with known indicator genes and systems for detecting their transcription and any of such genes can be effectively used to monitor activity of the inducible promoter of the present invention. For example, three commonly used detection systems rely upon the lacZ gene, luciferase gene, and the Green Fluorescent Protein gene.

The detected molecule can be formaldehyde if the attached indicator gene is gene is a Class III alcohol dehydrogenase enzyme, also called a "glutathione-dependent formaldehyde-dehydrogenase" or "GSH-FDHI" enzyme capable of dehydrogenating formaldehyde to other byproducts. Such genes are preferred indicator genes for use in a formaldehyde remediation method. Many such GSH-FDH genes are known and have been isolated from bacterial and eukaryotic sources. GSH-FDH genes having activity against formaldehyde are described, for example by Jornvall, H. et al., *Eur. J. Biochem.* 167:195 (1987), by Koivusalo, M. and L. Uotila, in *Enz. and Mol. Biol. of Carbonyl Metabolism* 3 and 4, Plenum Press, NY, eds. H. Weiner et al. (1990), by Engeland, K. et al., *Proc. Natl. Acad. Sci. USA* 90:2491 (1993), by Green, et al., *J.B.C.* 268:7792 (1993), and by Estonius, M. et al., *Biochemistry* 33:15080 (1994), all of which are incorporated herein by reference. Certain of these publications also describe the modification of other genes by point mutation to bring about formaldehyde-specific activity. Thus, not only are the classic GSH-FDH enzymes suitable for linkage to the promoter, but it will also be understood that other alcohol dehydrogenases, suitably modified can also be used in a formaldehyde remediation system. The source of the gene is not limiting, as long as the protein encoded by the gene is made and folded to form a protein that functions as desired in a bacterial host cell. Any such GSH-FDH gene that can be expressed in a bacterial host and which confers formaldehyde-specific dehydrogenating activity is acceptable. GSH-FDH enzymes also have activity against long chain hydroxylated fatty acids having between 8 and 16 carbons (e.g., 12-hydroxydodecanoic acid) and long chain alcohols having an alcohol group (OH) at the terminal carbon. The system disclosed herein could be adapted to reduce levels of such materials as well.

A suitable GSH-FDH gene is the adhI formaldehyde dehydrogenase gene of *Rhodobacter sphaeroides* which is co-regulated in vivo with a downstream gene encoding isocytochrome $c_2$ (cycI). The sequence of the adhI gene is shown herein as bases 346–1476 of SEQ. ID. NO:1. An arginine residue corresponding to the arginine at position 110 of AdhI has been shown to be important for enzymatic activity of other GSH-FDH enzymes against some substrates (including formaldehyde) and may be important to the activity of this gene product as well. Furthermore, AdhI has nine out of ten residues predicted to be conserved in the substrate binding cleft of GSH-FDH enzymes.

The adhI gene can be varied by addition, deletion or mutation of sequences that do not affect formaldehyde dehydrogenation. As evidence of the variation that is acceptable in such genes, *Rhodobacter sphaeroides adhI* contains an 18 nucleotide long insertion (bases 1111–1128) relative to known eukaryotic GSH-FDH genes that does not alter the ability of the encoded enzyme to oxidize formaldehyde.

It is understood by those of ordinary skill that certain variation in the size or sequence of the repressor or sensor components (and in the corresponding genetic material encoding the components), including for example allelic variants and mutations thereof, will not interfere with the functions thereof. Given the well understood degeneracy of the genetic code, a person of ordinary skill in the art understands that many other nucleotide sequences can encode the same amino acid sequence and all such nucleotide sequences that encode proteins having at least 90% identity, preferably at least 95% identity to the exemplified sequences (when compared using sequence alignment software such as that available from Genetics Computer Group, Madison, Wis.) and which retain the indicated repressor or sensor function are understood to fall within the scope of the invention. Such changes, modifications, dditions and deletions are contemplated to fall within the cope of the present invention, as long as the sensor components retain appropriate formaldehyde-sensing and effector portions and the repressor retains the ability to interact with the promoter/operator as described.

The competence of the inducible system can be judged by any measure of increased transcription of the operably linked indicator gene. Increased transcription can be measured directly by measuring RNA level, or indirectly by observing an increase in the level of the protein encoded by the indicator gene. Alternatively, a change in an indicator molecule affected by the attached gene can be measured. Such a change can be in color, concentration, fluorescence, optical density or other attribute.

The preferred promoter DNA, repressor coding sequence (and corresponding protein sequence), and sensor coding sequences (and corresponding protein sequences) were isolated and purified from the genome of wild type *Rhodobacter sphaeroides*. It is believed that with the guidance of the specification, especially the sequence data of SEQ ID NOS: 3–6, the promoter, the sensor, and/or the repressor of the formaldehyde-inducible system of the present invention can now readily be purified from other organisms capable of growth on formaldehyde or on a carbon source that can be degraded to formaldehyde, such as methanol, using routine techniques of molecular biology for isolating nucleic acids. Thus, the invention is not limited to these molecules prepared or obtained from a particular source. Rather, one of ordinary skill, using routine techniques for locating structurally related DNA (e.g., hybridization to a suitable probe under stringent conditions), can prepare a sequence specific probing strategy, employing, e.g. PCR analysis, to retrieve these sequences from other *Rhodobacter sphaeroides* strains, other Rhodospirillaceae, other bacterial organisms, and a wide variety of eukaryotic organisms known to have mechanisms for formaldehyde oxidation.

Formaldehyde oxidation is ubiquitous and GSH-FDH enzymes are found in many organisms. Such organisms are considered likely to contain such GSH-FDH genes and may contain the regulatory genes as well. Also, formaldehyde dehydrogenase activity has been observed in formaldehyde-resistant Enterobacteriaceae. Kaulfer, P. and A. Marquardt, FEMS Microbiol. Letters 79:335–338 (1991).

Bacterial, plant, yeast, and animal (including human) GSH-FDH enzymes have been shown to catalyze the AND-dependent oxidation of HMGSH and long chain hydroxylated fatty acids and alcohols. The nucleic acid sequence of a GSH-FDH gene from *Paracoccus denitrificans* has recently been reported by Ras, et al., J. Bact. 177:247–251 (1995), that shares 89% amino acid identity and 95% amino acid similarity to AdhI of *Rhodobacter sphaeroides*, and is predicted to be a useful effector gene for linkage to the inducible promoter of this system.

While identical sequences isolated from a different organism would certainly come within the scope of the present invention, it is also understood that complete structural relatedness is not necessary. As has been described above for each element, only that level of structural relatedness sufficient to maintain the functionality of the invention is required. It is contemplated and understood that certain nucleic acid substitutions in the operator, promoter, indicator gene, sensor gene and repressor gene have no effect or only moderate effect upon protein production and function. Indeed, given the well understood redundancy in the genetic code, certain nucleic acid substitutions are completely silent with respect to encoded protein sequences. All such substitutions to any of the various genetic constructs and proteins described herein are within the scope of the present invention.

It is not necessary that the components of the formaldehyde-inducible expression system be obtained from a single source, but rather, individual elements can be obtained from disparate sources or can be synthesized in vitro. It is also understood that, although the sequences presented herein are the preferred sequences known to the inventors for carrying out the invention, it is specifically envisioned that strains carrying mutations in any element of the system may be sought, using techniques available to those skilled in the art, to optimize the effect of the described expression system upon the promoter.

It is also envisioned that on the basis of this disclosure, the genetic components of this expression system can be created or combined in any combination in vitro using well understood tools available to a molecular biologist. It is routine to construct an expressible gene construct incorporating a promoter operably linked upstream (5') to a coding region encoding an indicator protein of interest. A suitable promoter sequence is provided which can direct the inducible transcription of any attached gene. To achieve the desired inducible regulatory effect in the disclosed system, it is desirable, in the uninduced state, that there be virtually no transcription of the gene of interest. Accordingly, it is desired that an amount of the repressor be available to effectively keep the promoter inactive in bacterial host cells in which the system is operative. Thus, expression of the gene encoding the repressor can be under the transcriptional control of a constitutive promoter. Since the sensor protein is required to sense formaldehyde in the environment and since the regulatory system does not induce appreciable transcription until formaldehyde is detected, the gene encoding the sensor protein can also be expressed constitutively in the bacterial host cells and can be under the transcriptional control of any promoter that can direct the transcription of the repressor protein. A suitable promoter can be determined for each strain into which the system will be introduced. For example, the *E. coli* $P_{lac}$ promoter is functional in many, but not all, bacterial cell hosts.

It is further envisioned that if the expression system of the present invention is incorporated into a larger regulatory scheme, it is certainly possible to regulate the expression of the sensor or regulatory proteins as desired by selecting other promoters to govern transcription in a non-constitutive manner.

The present invention will be more completely understood upon consideration of the following Examples which are intended to be exemplary and in no way limiting on the invention.

EXAMPLES
Bacterial Strains, Plasmids and Growth Conditions.

R. sphaeroides strains were grown in Sistrom's minimal medium A (37) at 32° C. Supplements were sterilized separately and added at the following concentrations: ampicillin, 100 µg/ml; tetracycline, 1 µg/ml for R. sphaeroides; spectinomycin, 25 µg/ml/ and isopropyl-β-D-thiogalactopyranoside (IPTG), 1 mM.

A spontaneous mutant Rhodobacter sphaeroides that overexpresses the AdhI gene and can grow photosynthetically was the recipient of cosmid pUI8017. Upon addition of the cosmid (which contains the complete repressor/sensor operon) in multiple copies, the host cell was no longer able to grow photosynthetically because of the presence of the repressor protein encoded on the cosmid.

DNA Sequence Analysis

DNA sequencing was performed either with Taq DNA polymerase (Promega, Inc., Madison, Wis.) with deaza nucleoside triphosphate reagent kits or using an automated sequencer. Most of the DNA sequence was obtained with lac specific primers and double-stranded derivatives of pUC18 or pUC19 vectors. Primers specific to R. sphaeroides DNA were used to aid in analyzing regions with strong secondary structure or to complete the generation of double-stranded DNA sequence. DNA and the subsequent protein sequence were analyzed with software from Genetics Computer Group, Madison, Wis. The DNA sequence fragment from the BamHI to SalI restriction endonuclease sites shown in FIG. 1 (SEQ ID NO: 1) is available at Genbank accession number L47326.

GSH-FDH Activity Assays

GSH-FDH activity can be detected in crude cell extracts using the following detection scheme. Cultures of R. sphaeroides cells were grown aerobically to late log-early stationary phase, harvested (8,000×g), and washed with 150 mM sodium phosphate buffer (pH 8.5). Cell pellets were stored at −20° C. until the assay was performed. Prior to lysis, the thawed cell pellet was suspended in 5 ml of 150 mM sodium phosphate buffer (pH 8.5) containing 0.1% phenylmethylsulfonylfluoride as a protease inhibitor. The cells were lysed by two passes through a French press at 18,000 psi, DNase was added to a final concentration of 5 µg/ml, and the lysate was incubated on ice for 30 minutes. Cell debris was removed by centrifugation at 10,000×g for minutes and the supernatant was assayed for GSH-FDH activity. Protein concentrations was determined by the SDS modification of the Folin phenol method using bovine serum albumin as a standard.

Assays for GSH-FDH activity using S-hydroxy methylglutathione (HMGSH) as a substrate were performed as described by Uotila and Koviusalo, Methods Enzymol. 77:314–320 (1981), with the following modifications: the final concentration of sodium phosphate buffer (pH 8.5) is 150 mM, the final concentration of AND was 1 mM, and 0.01 to 1 mg of crude cell extract protein was added. A typical assay using other potential GSH-FDH substrates includes a volume of cell extract (containing 0.1 to 1 mg total protein), 150 mM sodium phosphate buffer (pH 8.5), 1 mM AND as an electron acceptor, and appropriate concentration of substrate [1 mM for long chain (>5 aliphatic carbons) alcohols and acids, 0.2 M to 1 M for short chain (<5 aliphatic carbons) alcohols]. In all cases, enzyme activity was measured spectrophotometrically by the time-dependent reduction of AND and corresponding increase in absorbance at 340 nm at room temperature using a SLM DW2000 spectrophotometer. A unit of GSH-FDH activity is defined as the amount of enzyme required to reduce 1 µmole of AND per minute.

The size of an active GSH-FDH protein was determined by activity gel electrophoresis. Following native polyacrylamide gel electrophoresis, zymograms for GSH-FDH activity were obtained by adding a half volume of a loading solution, containing 40% (w/v) sucrose plus a trace of bromophenol blue to an appropriate volume of cell extract prior to loading the gel. Proteins were separated on a 5% stacking gel and 10% separating gel using Tris-HCl buffer (pH 8.3) in the gel and Tris-glycine buffer (pH 8.8) in the electrode vessels with an applied current of 10–20 mA/gel at 4° C. for a minimum of 14 hours.

Following electrophoresis, the gel was stained for GSH-FDH activity using a solution of 70 mM sodium phosphate buffer (pH 7.5); 500 mM KCl; 1.2 mM AND; 4.8 mM formaldehyde; 1 mM glutathione; 0.4 mg/ml nitroblue tetrazolium and 0.03 mg/ml phenylmethylsulfate with gentle shaking at 37° C. Enzyme activity was visualized in less than an hour and the gel was rinsed in distilled water prior to photographing.

Promoter Isolation

The location of the promoters upstream from the R. sphaeroides adhI gene were determined by primer extension analysis. RNA from aerobic R. sphaeroides cultures was prepared as previously described by Zhu and Kaplan, J. Bacteriol. 162:925–932 (1985). An oligonucleotide (4'-ATTGACCTCCATGATCTCGA-3') (SEQ ID NO: 7) complementary to a region 42 nucleotides downstream of the adhI translational start codon was used for primer extension assays (Genosys, The Woodlands, Tex.). Primer (25 pmole) and RNA (15 µg) were hybridized at 45° C. for 15 minutes; then a solution of nucleotide triphosphates, reverse transcriptase, and actinomycin D was added and incubated for 30 minutes at 45° C. The reaction was stopped by adding a formamide-EDTA loading buffer. Samples were boiled prior to loading on a 6% denaturing polyacrylamide gel. Putative transcription initiation sites were mapped by comparison to DNA sequencing reactions generated with the same primer on an adhI template.

Preference for Induction by Formaldehyde

Figure 3:
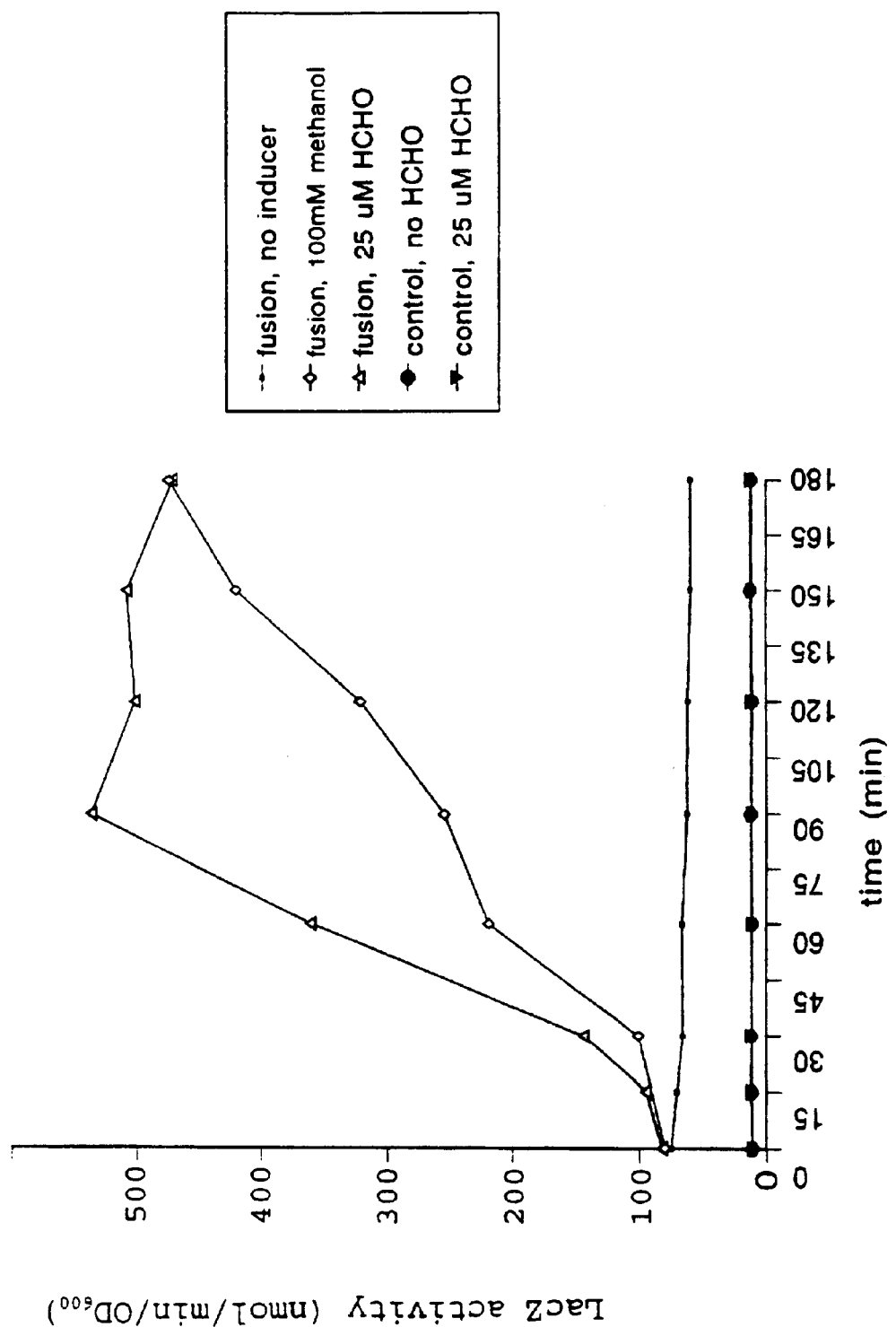
FIG. 3 depicts induction by methanol and formaldehyde of an indicator gene (lacZ) operably linked to the promoter and operator described herein.

FIG. 3 depicts the activity of the full-length adhI promoter when the promoter is fused to an indicator gene (lacZ). Wild type Rhodobacter sphaeroides cells carrying the full length adhI promoter region fused to lacZ on a plasmid were grown to mid-log phase. Then, either methanol or formaldehyde was added to the media and beta-galactosidase was measured during a three hour time course. Without any inducer, activity of LacZ encoded by the test construct was low and invariant over time. In contrast, in the presence of 25 µM formaldehyde, the lacZ gene was induced to produce as much as about 425 lacZ activity units (nMol/min/OD600) by about 90 minutes. This rate was maintained for at least another 1.5 hours. Using 100 mM methanol as the inducer, it took almost 3 hours to reach this level of LacZ activity.

To demonstrate the specificity of the response, the control included a cycA gene operably fused to the E. coli lacZ gene.

What is claimed is:

1. A method for oxidizing formaldehyde in a sample, the method comprising the steps of:
   providing a *Rhodobacter sphaeroides* bacterial cell that comprises a glutathione S-transferase/formaldehyde dehydrogenase (GSH-FDH) gene, a transcriptional adhI promoter from *Rhodobacter sphaeroides* operably linked to the GSH-FDH gene, a cis-acting operator from *Rhodobacter swhaeroides* operably linked to the promoter, at least one protein that senses formaldehyde, and a trans-acting regulatory protein that modulates transcription of the GSH-FDH gene from the transcriptional promoter in response to a signal from the protein that senses formaldehyde, wherein the promoter and the operator together specifically direct transcription of the GSH-FDH gene when the cell is exposed to formaldehyde;
   adding the bacterial cell to the sample; and
   detecting a decrease in formaldehyde in the sample.

2. A method as claimed in claim 1 wherein the bacterial cell further comprises a polynucleotide sequence that encodes at least one protein that senses formaldehyde.

3. A method as claimed in claim 1 wherein the cell further comprises a polynucleotide sequence that encodes the trans-acting regulatory protein.

4. A method as claimed in claim 1 wherein the GSH-FDH gene is *Rhodobacter sphaeroides* adhI.

5. A method as claimed in claim 1 wherein the transcriptional promoter is located within the sequence between nucleotides 241 and 310 of SEQ ID NO:1.

6. A method as claimed in claim 1 wherein the transcriptional promoter is located within the sequence between nucleotides 220 and 310 of SEQ ID NO:1.

7. A method as claimed in claim 1 wherein the transcriptional promoter is located within the sequence between nucleotides 1 and 310 of SEQ ID NO:1.

8. A method as claimed in claim 1 wherein the operator comprises the sequence shown between bases 289 to 310 of SEQ ID NO:1.

9. A method as claimed in claim 2 wherein the polynucleotide sequence that encodes at least one protein that senses formaldehyde is selected from the group consisting of SEQ ID NO:3 from bases 993 to 2165, SEQ ID NO:3 from bases 2236 to 4427, and a variant thereof that encodes a protein that transduces a signal in the presence of formaldehyde.

10. A method as claimed in claim 2 wherein the polynucleotide sequence comprises SEQ ID NO:3 from bases 993 to 2165 and SEQ ID NO:3 from bases 2236 to 4427.

11. A method as claimed in claim 3 wherein the polynucleotide sequence that encodes the trans-acting regulatory protein is selected from the group consisting of bases 215 to 895 of SEQ ID NO:3, and a variant thereof that encodes a protein that modulates transcription from a transcriptional promoter that comprises a sequence between nucleotides 220 and 310 of SEQ ID NO:1.

12. A method as claimed in claim 4 wherein the GSH-FDH gene comprises the sequence between nucleotides 346 and 1476 of SEQ ID NO:1.

13. A method as claimed in claim 11 wherein the cell further comprises a polynucleotide sequence that encodes at least one protein that senses formaldehyde, the polynucleotide sequence being selected from the group consisting of SEQ ID NO:3 from bases 993 to 2165 and SEQ ID NO:3 from bases 2236 to 4427.

14. A method as claimed in claim 12 wherein the polynucleotide sequence encoding at least one protein that senses formaldehyde comprises SEQ ID NO:3 from bases 993 to 2165 and SEQ ID NO:3 from bases 2236 to 4427.

* * * * *

UNITED STATES PATENT AND TRADEMARK OFFICE
CERTIFICATE OF CORRECTION

PATENT NO.    : 6,242,244 B1
DATED         : June 5, 2001
INVENTOR(S)   : Timothy Donohue, Robert Barber, and Vernon Witthuhn Page 1 of 1

It is certified that error appears in the above-identified patent and that said Letters Patent is hereby corrected as shown below:

<u>Column 1,</u>
Lines 13 through 16, delete and insert therefor:
-- This invention was made with United States government support awarded by the following agencies:
DOE Grant No: DE-FG02-97ER20262
NIH Grant No: GM37509
USDA HATCH 3766
The United States Government has certain rights in this invention. --

Signed and Sealed this

Twenty-ninth Day of January, 2002

Attest:

JAMES E. ROGAN
*Attesting Officer*    *Director of the United States Patent and Trademark Office*

SEQUENCE LISTING

<160> NUMBER OF SEQ ID NOS: 7

<210> SEQ ID NO 1
<211> LENGTH: 2408
<212> TYPE: DNA
<213> ORGANISM: Rhodobacter sphaeroides
<220> FEATURE:
<221> NAME/KEY: -35_signal
<222> LOCATION: (262)..(267)
<220> FEATURE:
<221> NAME/KEY: -10_signal
<222> LOCATION: (285)..(290)
<220> FEATURE:
<221> NAME/KEY: CDS
<222> LOCATION: (346)..(1476)

<400> SEQUENCE: 1

```
gatccgcgcg gctgcgcgag ctggggctcg agccctacga tgcgctctcg ccgcccctga       60
tggatgcgat cgcgacccat gtcgcgaaac gctccggcaa gctcgcggcc tgagggctgc      120
ggccgctccc tcccgcgagg cggggagcgg cttcttctga acgtgccggg cgcggtccga      180
tggcggcagg cctgccgacg cgggaccccc gcaggctttc gccgcagagg caagacccgc      240
gctcctcatc ctttttccg  aatgccgggc gcggattttc ctcttaaggt caggccatga      300
caggcccgac gccctgccgt ccggttgatt gagagggaga gtaac atg cgc acc cgt      357
                                                 Met Arg Thr Arg
                                                   1
```

```
gcc gcc gtc gcc gtc gag gcc ggc aag ccg ctc gag atc atg gag gtc      405
Ala Ala Val Ala Val Glu Ala Gly Lys Pro Leu Glu Ile Met Glu Val
  5                  10                  15                  20 aat ctc gaa ggc ccc aag gcc ggc gag gtc atg gtc gag atc aag gcc      453
Asn Leu Glu Gly Pro Lys Ala Gly Glu Val Met Val Glu Ile Lys Ala
                 25                  30                  35 acc ggc atc tgc cac acc gac gaa ttc acc ctc tcc ggc gcc gat ccc      501
Thr Gly Ile Cys His Thr Asp Glu Phe Thr Leu Ser Gly Ala Asp Pro
         40                  45                  50 gag ggc atg ttc ccg gcg atc ctc ggc cac gag ggc gcg ggc gtg gtg      549
Glu Gly Met Phe Pro Ala Ile Leu Gly His Glu Gly Ala Gly Val Val
     55                  60                  65 gtc gag gtc ggc ccc ggc gtg acc agc gtg aag ccc ggc gat cat gtg      597
Val Glu Val Gly Pro Gly Val Thr Ser Val Lys Pro Gly Asp His Val
 70                  75                  80 atc ccg ctc tac acg ccc gag tgc cgg cag tgc ccc tcc tgc ctc agc      645
Ile Pro Leu Tyr Thr Pro Glu Cys Arg Gln Cys Pro Ser Cys Leu Ser
 85                  90                  95                 100 cag aag acg aac ctc tgc acc gcg atc cgc ggc acg cag ggg cag ggg      693
Gln Lys Thr Asn Leu Cys Thr Ala Ile Arg Gly Thr Gln Gly Gln Gly
                105                 110                 115 ctg atg ccc gac ggc acc agc cgc ttc tcg atg ctc gat ggc acg ccg      741
Leu Met Pro Asp Gly Thr Ser Arg Phe Ser Met Leu Asp Gly Thr Pro
            120                 125                 130 atc ctg cat tac atg ggc tgc tcg acc ttc tcg aac tac acg gtc ctg      789
Ile Leu His Tyr Met Gly Cys Ser Thr Phe Ser Asn Tyr Thr Val Leu
        135                 140                 145 ccc gag atc gcg gtg gcg aag gtg cgc ccg gat gcg ccc ttc gac aag      837
Pro Glu Ile Ala Val Ala Lys Val Arg Pro Asp Ala Pro Phe Asp Lys
    150                 155                 160 atc tgc tac atc ggc tgc ggc gtc acc acc ggc atc ggc gcg gtc atc      885
Ile Cys Tyr Ile Gly Cys Gly Val Thr Thr Gly Ile Gly Ala Val Ile
165                 170                 175                 180
```

```
aac acg gcc aag gtc gag atc ggc gcc aag gcc gtg gtg ttc ggg ctg          933
Asn Thr Ala Lys Val Glu Ile Gly Ala Lys Ala Val Val Phe Gly Leu
                185                 190                 195 ggc ggc atc ggt ctc aac gtg atc cag ggc ctg aag ctc gcg ggc gcc          981
Gly Gly Ile Gly Leu Asn Val Ile Gln Gly Leu Lys Leu Ala Gly Ala
            200                 205                 210 gac atg atc atc ggc gtg gat ctg aac aac gcc aag aag gaa tgg ggc         1029
Asp Met Ile Ile Gly Val Asp Leu Asn Asn Ala Lys Lys Glu Trp Gly
                215                 220                 225 gag cgc ttc ggc atg acc cat ttc gtg aat ccg tcc gag atc gac ggc         1077
Glu Arg Phe Gly Met Thr His Phe Val Asn Pro Ser Glu Ile Asp Gly
        230                 235                 240 gat gtg gtg gcg cat ctg gtc aat atg acc aag acg ccc ttc gac cag         1125
Asp Val Val Ala His Leu Val Asn Met Thr Lys Thr Pro Phe Asp Gln
245                 250                 255                 260 atc ggc ggg gcg gac tac acc ttc gac tgc acc ggc aac gtg aag gtg         1173
Ile Gly Gly Ala Asp Tyr Thr Phe Asp Cys Thr Gly Asn Val Lys Val
                265                 270                 275 atg cgt cag gcg ctg gag gcg tgc cat cgt ggc tgg ggc cag tcg atc         1221
Met Arg Gln Ala Leu Glu Ala Cys His Arg Gly Trp Gly Gln Ser Ile
            280                 285                 290 gtg atc ggt gtg gcg ccg gcg ggg gcc gag atc cag acg cgg ccg ttc         1269
Val Ile Gly Val Ala Pro Ala Gly Ala Glu Ile Gln Thr Arg Pro Phe
                295                 300                 305 cag ctg gtg acg ggg cgg gtc tgg aag ggc tcg gcc ttc ggc ggc gcg         1317
Gln Leu Val Thr Gly Arg Val Trp Lys Gly Ser Ala Phe Gly Gly Ala
        310                 315                 320 cgc ggc cgg acc gac gtg ccg aag atc gtc gac tgg tac atg gag ggc         1365
Arg Gly Arg Thr Asp Val Pro Lys Ile Val Asp Trp Tyr Met Glu Gly
325                 330                 335                 340 aag atc cag atc gac ccg atg atc acc cac atc ctg agc ctc gaa gag         1413
Lys Ile Gln Ile Asp Pro Met Ile Thr His Ile Leu Ser Leu Glu Glu
                345                 350                 355 atc aac aag ggc ttc gac ctc atg cac gcg ggc gag tcc atc cgc tcg         1461
Ile Asn Lys Gly Phe Asp Leu Met His Ala Gly Glu Ser Ile Arg Ser
            360                 365                 370 gtc gtg gtg ttc tga tcggccaccc ctccaagacg gtgacgattt cccgagtaac         1516
Val Val Val Phe
            375 ggtgccagcg acccggccgg tcccttgacc ggccgcgggc ggcctgccgc gcaggacgcc       1576 cccgagccat ccgcaaaggg agaagaccat gagattgacc accatcctcg ccggggcgct       1636 cgctctcggt gccgcgcagg ccgccttcgc cgaaggcgac ccggcggccg gcgagaaggc       1696 cttccggaaa tgtcaggcct gccaccagat cggcgccgag gcgcagaaca agaccgggcc       1756 cgtcctgacc ggcgtcatcg gtcgcccggc ggcctcgatc gagggcttca gctattccaa       1816 gaccctgacc gaggccgcgg ccgatggcct cgtctgggat catgctgcgc tcgagacctt       1876 cctggccaat ccgcgcaagg cgatgccggg caccaagatg gccttccccg gcatcaagaa       1936 accgcaggag ctggccgaca tcctggccta tctcgacacc ttctcggacg gggaaacgcg       1996 ggaggccgaa gagacccccg cggcggcgcc ggcggagggc tgaaatgcct gtctgccaag       2056 gctttcgccc tcgtcatggc gccaccggcg atcgtcatac tttgggctta aagcgggacc       2116 gcagcgttaa cgcttcaaat cggcgcgccg tagcatgagg ttcggtgaca ggtcggcagc       2176 tccggggagg gagccgcgac cggtgaagat cacgagccaa tttcaagaaa tcaacatcgg       2236 gaggagccaa tgaagatgct gaagacgggt ctcgtagcga ccctattgct ctcgtctcgc       2296 ggccagaacg gttgctgagc caggagttcc gctggctgct aggcttcgtc acccgctagg       2356
```

-continued

```
tctggccgct tgatacggtt gtgggcgata aggctcgact tggtctagtg gg          2408
```

<210> SEQ ID NO 2
<211> LENGTH: 376
<212> TYPE: PRT
<213> ORGANISM: Rhodobacter sphaeroides

<400> SEQUENCE: 2

```
Met Arg Thr Arg Ala Ala Val Ala Val Glu Ala Gly Lys Pro Leu Glu
  1               5                  10                  15

Ile Met Glu Val Asn Leu Glu Gly Pro Lys Ala Gly Glu Val Met Val
             20                  25                  30

Glu Ile Lys Ala Thr Gly Ile Cys His Thr Asp Glu Phe Thr Leu Ser
         35                  40                  45

Gly Ala Asp Pro Glu Gly Met Phe Pro Ala Ile Leu Gly His Glu Gly
     50                  55                  60

Ala Gly Val Val Glu Val Gly Pro Gly Val Thr Ser Val Lys Pro
 65                  70                  75                  80

Gly Asp His Val Ile Pro Leu Tyr Thr Pro Glu Cys Arg Gln Cys Pro
                 85                  90                  95

Ser Cys Leu Ser Gln Lys Thr Asn Leu Cys Thr Ala Ile Arg Gly Thr
            100                 105                 110

Gln Gly Gln Gly Leu Met Pro Asp Gly Thr Ser Arg Phe Ser Met Leu
        115                 120                 125

Asp Gly Thr Pro Ile Leu His Tyr Met Gly Cys Ser Thr Phe Ser Asn
    130                 135                 140

Tyr Thr Val Leu Pro Glu Ile Ala Val Ala Lys Val Arg Pro Asp Ala
145                 150                 155                 160

Pro Phe Asp Lys Ile Cys Tyr Ile Gly Cys Gly Val Thr Thr Gly Ile
                165                 170                 175

Gly Ala Val Ile Asn Thr Ala Lys Val Glu Ile Gly Ala Lys Ala Val
            180                 185                 190

Val Phe Gly Leu Gly Gly Ile Gly Leu Asn Val Ile Gln Gly Leu Lys
        195                 200                 205

Leu Ala Gly Ala Asp Met Ile Ile Gly Val Asp Leu Asn Asn Ala Lys
    210                 215                 220

Lys Glu Trp Gly Glu Arg Phe Gly Met Thr His Phe Val Asn Pro Ser
225                 230                 235                 240

Glu Ile Asp Gly Asp Val Val Ala His Leu Val Asn Met Thr Lys Thr
                245                 250                 255

Pro Phe Asp Gln Ile Gly Gly Ala Asp Tyr Thr Phe Asp Cys Thr Gly
            260                 265                 270

Asn Val Lys Val Met Arg Gln Ala Leu Glu Ala Cys His Arg Gly Trp
        275                 280                 285

Gly Gln Ser Ile Val Ile Gly Val Ala Pro Ala Gly Ala Glu Ile Gln
    290                 295                 300

Thr Arg Pro Phe Gln Leu Val Thr Gly Arg Val Trp Lys Gly Ser Ala
305                 310                 315                 320

Phe Gly Gly Ala Arg Gly Arg Thr Asp Val Pro Lys Ile Val Asp Trp
                325                 330                 335

Tyr Met Glu Gly Lys Ile Gln Ile Asp Pro Met Ile Thr His Ile Leu
            340                 345                 350

Ser Leu Glu Glu Ile Asn Lys Gly Phe Asp Leu Met His Ala Gly Glu
        355                 360                 365
```

```
Ser Ile Arg Ser Val Val Val Phe
    370             375

<210> SEQ ID NO 3
<211> LENGTH: 4826
<212> TYPE: DNA
<213> ORGANISM: Rhodobacter sphaeroides
<220> FEATURE:
<221> NAME/KEY: CDS
<222> LOCATION: (215)..(895)
<220> FEATURE:
<221> NAME/KEY: CDS
<222> LOCATION: (993)..(2165)
<220> FEATURE:
<221> NAME/KEY: CDS
<222> LOCATION: (2236)..(4437)

<400> SEQUENCE: 3
ggatccgggc atgcctgcgg ccgaaggatg cgggaaccgc tccgcaccga cagatgcgcg      60
aaccgtatgg ccggccggga agtgggggc tccgcctctc tcggtaagaa caggtcggtg     120
cgccgtagcg gcaagggcgc cggtgctccg acctttggcc gggttatcgc gtcaggcgga    180
tgtgctagcc tcgtgaaaag acgtatggga ccgc atg atc gaa cct tcc cgc ccg    235
                                     Met Ile Glu Pro Ser Arg Pro
                                       1               5 ctc cag tcc gcg ctg atc gtc gac gat cat ccg ctc ttc tgc gat gcg      283
Leu Gln Ser Ala Leu Ile Val Asp Asp His Pro Leu Phe Cys Asp Ala
         10                  15                  20 ctg tcg atg acg ctc aag gcg gtg gcg gga ctg acc cac atc gaa tcc      331
Leu Ser Met Thr Leu Lys Ala Val Ala Gly Leu Thr His Ile Glu Ser
     25                  30                  35 gcc gac cgg ctc gag acg gct ctg gcc cgg ctc gac ctg cag ccg gcg      379
Ala Asp Arg Leu Glu Thr Ala Leu Ala Arg Leu Asp Leu Gln Pro Ala
 40                  45                  50                  55 ttc gat gtg gtg gtg ctg gat ctg aac ctg ccg gac gtg aac ggc ctc      427
Phe Asp Val Val Val Leu Asp Leu Asn Leu Pro Asp Val Asn Gly Leu
                 60                  65                  70 gac ggc ctc atc cgt ctg aag gcg agc ctc ggg gcg gtg ccg gtg gtg      475
Asp Gly Leu Ile Arg Leu Lys Ala Ser Leu Gly Ala Val Pro Val Val
             75                  80                  85 gtg gtc tct tcc ctc gcc gac aac cgg gtg atc ggg gcg gcg ctg aag      523
Val Val Ser Ser Leu Ala Asp Asn Arg Val Ile Gly Ala Ala Leu Lys
         90                  95                 100 gcg ggt gcg gcg ggc ttc gtg ccc aag cac tcc cgc cgc gag gtg ttc      571
Ala Gly Ala Ala Gly Phe Val Pro Lys His Ser Arg Arg Glu Val Phe
    105                 110                 115 cgc gcg gcc ttc gat gcg atc cgc gaa ggg cgc agc tac ctg ccc gaa      619
Arg Ala Ala Phe Asp Ala Ile Arg Glu Gly Arg Ser Tyr Leu Pro Glu
120                 125                 130                 135 gga ttc acg cct cat tcc ccc ggc gcg ccc gcc agc cag cgc gag gaa      667
Gly Phe Thr Pro His Ser Pro Gly Ala Pro Ala Ser Gln Arg Glu Glu
                140                 145                 150 gcc atc gca cgg ctt gcg ctg ctc acg cgg cag cag gcg aag atc ctc      715
Ala Ile Ala Arg Leu Ala Leu Leu Thr Arg Gln Gln Ala Lys Ile Leu
            155                 160                 165 cag ctc atc tgc gag ggg cgg ctg aac aag cag atc gcc tat gac ctg      763
Gln Leu Ile Cys Glu Gly Arg Leu Asn Lys Gln Ile Ala Tyr Asp Leu
        170                 175                 180 acc atc gcc gag acg acc gtg aag gcc cat gtc acg gcc atc atg cgc      811
Thr Ile Ala Glu Thr Thr Val Lys Ala His Val Thr Ala Ile Met Arg
    185                 190                 195
```

-continued

| | |
|---|---|
| aag ctc ggc gtc cag agc cgg acc cag gcg gtg ctc atg gtg cag gag<br>Lys Leu Gly Val Gln Ser Arg Thr Gln Ala Val Leu Met Val Gln Glu<br>200                        205                    210                      215 | 859 |
| gcg agc ttc gcg agc ctg atg ccg gaa aat tcc tga cagccggttg<br>Ala Ser Phe Ala Ser Leu Met Pro Glu Asn Ser<br>                    220                      225 | 905 |
| ggcagcggct gcgcgcttcg ggggcctgtc gaacggcttg tcagccgtgc gggcacgaga | 965 |
| ttaggtttgc tggctgggag gacggcg atg gaa gga ctg cgc gag cgg gcg gtc<br>                                                    Met Glu Gly Leu Arg Glu Arg Ala Val<br>                                                             230                              235 | 1019 |
| gcg gcg gag cgg aac ggc gcc ccg ctg gtg cgg agc gcc cat ctg ccc<br>Ala Ala Glu Arg Asn Gly Ala Pro Leu Val Arg Ser Ala His Leu Pro<br>                    240                        245                      250 | 1067 |
| gga gac gtg ccc gca gcc gca gag cgg ctg gcg gaa gct ctg ggc gag<br>Gly Asp Val Pro Ala Ala Ala Glu Arg Leu Ala Glu Ala Leu Gly Glu<br>                    255                        260                      265 | 1115 |
| ggg ccg ttc gcc ctc gtg atc ctg ttc gtg acg ccc gag acc gac gtg<br>Gly Pro Phe Ala Leu Val Ile Leu Phe Val Thr Pro Glu Thr Asp Val<br>270                        275                    280 | 1163 |
| tcg gcc ctc gcc ctc ggg gcg cag gag gtc ttc ggc ccc gtg ccg gtg<br>Ser Ala Leu Ala Leu Gly Ala Gln Glu Val Phe Gly Pro Val Pro Val<br>285                        290                    295                  300 | 1211 |
| atc ggc tgc acc acg gcc ggc gag atc agc gcc gag ggc tat acc gaa<br>Ile Gly Cys Thr Thr Ala Gly Glu Ile Ser Ala Glu Gly Tyr Thr Glu<br>                    305                        310                      315 | 1259 |
| ggc gag gtg gtg gcg gtg gcg ctt ccc gcc gcc cat ttc cac gtc cgg<br>Gly Glu Val Val Ala Val Ala Leu Pro Ala Ala His Phe His Val Arg<br>                    320                        325                      330 | 1307 |
| ccc atc ctg atc ggg gct ttg gcc gat ctc gac cgc gag gaa ctg atc<br>Pro Ile Leu Ile Gly Ala Leu Ala Asp Leu Asp Arg Glu Glu Leu Ile<br>335                        340                    345 | 1355 |
| ggc cgc ctc atc cgc gag cgg gat gcg ctg gcg cgc gag cgg ccc gac<br>Gly Arg Leu Ile Arg Glu Arg Asp Ala Leu Ala Arg Glu Arg Pro Asp<br>350                        355                    360 | 1403 |
| tgg ggc agc gaa ttc gcc ttc ctc atg gtg gac ggg ctg tcg acg cgc<br>Trp Gly Ser Glu Phe Ala Phe Leu Met Val Asp Gly Leu Ser Thr Arg<br>365                        370                    375                  380 | 1451 |
| gag gac gaa ctg gcc tcg acg ctc gcc gcg ggg ctg ggg ccg gtg ccg<br>Glu Asp Glu Leu Ala Ser Thr Leu Ala Ala Gly Leu Gly Pro Val Pro<br>                    385                        390                      395 | 1499 |
| ctc ttc ggc ggc tcg gcc gcc gac ggc gtg cgc ttc cgc gag acc ttc<br>Leu Phe Gly Gly Ser Ala Ala Asp Gly Val Arg Phe Arg Glu Thr Phe<br>                    400                        405                      410 | 1547 |
| gtg atc cat ggc gcc gat gtc ctg agg gac gcg gcg gtg ctg gcg ctg<br>Val Ile His Gly Ala Asp Val Leu Arg Asp Ala Ala Val Leu Ala Leu<br>                    415                        420                      425 | 1595 |
| gtg cgg agc gac tgc cgg gtg cgg gtg ttc aac ctc gac cat ttc cgc<br>Val Arg Ser Asp Cys Arg Val Arg Val Phe Asn Leu Asp His Phe Arg<br>430                        435                    440 | 1643 |
| ccc acc gat cag cgc atg gtc gtc acc gag gcc gat ccc gcg cgc cgc<br>Pro Thr Asp Gln Arg Met Val Val Thr Glu Ala Asp Pro Ala Arg Arg<br>445                        450                    455                  460 | 1691 |
| atc gtg cgc cgg atc aat gcc gag ccc gcg gcg cag gaa tat gcc cgg<br>Ile Val Arg Arg Ile Asn Ala Glu Pro Ala Ala Gln Glu Tyr Ala Arg<br>                    465                        470                      475 | 1739 |
| ctg ctc ggc aag gat ccg ggg cag ctc gac agc ttc acc ttc gcg gcc<br>Leu Leu Gly Lys Asp Pro Gly Gln Leu Asp Ser Phe Thr Phe Ala Ala<br>480                        485                    490 | 1787 |

```
cat ccg gtg gtg gtg cgg atc ggc ggc aag cat cac gtc cgc gcc atc    1835
His Pro Val Val Val Arg Ile Gly Gly Lys His His Val Arg Ala Ile
        495                 500                 505 cgc gag gtc gcg ccg aac gcg atc tcg ttc ttc ttt tcc gcc atc gac    1883
Arg Glu Val Ala Pro Asn Ala Ile Ser Phe Phe Phe Ser Ala Ile Asp
    510                 515                 520 gag ggg ctg gtg ctt gcg ctg gcc gaa ccg cag gat ctc gtc ggg cat    1931
Glu Gly Leu Val Leu Ala Leu Ala Glu Pro Gln Asp Leu Val Gly His
525                 530                 535                 540 ctg acg gac gag ctg gcg ggg ctg ggc gcg gag cgc gag ccc tcg gcc    1979
Leu Thr Asp Glu Leu Ala Gly Leu Gly Arg Glu Arg Glu Pro Ser Ala
                545                 550                 555 att gtc gcg tgc gat tgc gtg ctg cgc cgg atg gag gcg ctc gac agc    2027
Ile Val Ala Cys Asp Cys Val Leu Arg Arg Met Glu Ala Leu Asp Ser
            560                 565                 570 cag tcc atc ggg gcg gtc tcg gcc ctt ctg cgg cgg cat cgc gtg gtg    2075
Gln Ser Ile Gly Ala Val Ser Ala Leu Leu Arg Arg His Arg Val Val
        575                 580                 585 ggc ttc tcg acc tac ggc gag cag ctg aac ggg atg cat gtg aac cag    2123
Gly Phe Ser Thr Tyr Gly Glu Gln Leu Asn Gly Met His Val Asn Gln
    590                 595                 600 acc atg acc ggg gtc gcg atc tac ccg ccg gag gag cga tga            2165
Thr Met Thr Gly Val Ala Ile Tyr Pro Pro Glu Glu Arg
605                 610                 615 gggcgggccg gggcggtgac ctgcgtccca gtgggggaag gaccatgcgc cacgcggagc  2225
gggagcggac atg agc ctt gct ctg atc gat ccc agc gat ccg ccc gag    2274
           Met Ser Leu Ala Leu Ile Asp Pro Ser Asp Pro Pro Glu
               620                 625                 630 cga cag cgg gac aag ctt ctc gag atc gtg cgc gcg ctg atg gcg cgg    2322
Arg Gln Arg Asp Lys Leu Leu Glu Ile Val Arg Ala Leu Met Ala Arg
                635                 640                 645 gtg gag cgc acg acc gac gac ggc ggt gcg gcc tat gcg cag ttc cag    2370
Val Glu Arg Thr Thr Asp Asp Gly Gly Ala Ala Tyr Ala Gln Phe Gln
        650                 655                 660 cgc gcc gcc atg ctc gag gat cag gtg cgc gag cgc aca gcg gat ctg    2418
Arg Ala Ala Met Leu Glu Asp Gln Val Arg Glu Arg Thr Ala Asp Leu
    665                 670                 675 cag cgc acg ctg gaa ctg ctg aac ctc tcg aac gag cgg ctg gcg gaa    2466
Gln Arg Thr Leu Glu Leu Leu Asn Leu Ser Asn Glu Arg Leu Ala Glu
680                 685                 690                 695 gcc acg cgc gcg gcc gag gag gcg cgc cag aac ctc gcc aat gcc atc    2514
Ala Thr Arg Ala Ala Glu Glu Ala Arg Gln Asn Leu Ala Asn Ala Ile
                700                 705                 710 gag acg gtg cag gag ggc ttc gcg ctc ttc gat gcc gac gat gtg ctc    2562
Glu Thr Val Gln Glu Gly Phe Ala Leu Phe Asp Ala Asp Asp Val Leu
        715                 720                 725 gtg ctg tgc aat ttg cgc ttc ggg atg cac atg ctc gac att cag gag    2610
Val Leu Cys Asn Leu Arg Phe Gly Met His Met Leu Asp Ile Gln Glu
    730                 735                 740 cat ctg agg ccc ggc ctc tcc ttc ggc ggc tat atc gac cgc gtg agc    2658
His Leu Arg Pro Gly Leu Ser Phe Gly Gly Tyr Ile Asp Arg Val Ser
745                 750                 755 cgt tcg cgg tat ctg gcg ctg ccc gag gcg gag aca ccc gag gat tgg    2706
Arg Ser Arg Tyr Leu Ala Leu Pro Glu Ala Glu Thr Pro Glu Asp Trp
760                 765                 770                 775 gcg gtc cgg cgc aag cgg cgg cac tac gac cgg cat tcg atc ttc aac    2754
Ala Val Arg Arg Lys Arg Arg His Tyr Asp Arg His Ser Ile Phe Asn
                780                 785                 790
```

```
                                                              -continued gtg cgg ctg atc tgg gac cgc tgg ctg cag gtc tcc gag cat cgg acg     2802
Val Arg Leu Ile Trp Asp Arg Trp Leu Gln Val Ser Glu His Arg Thr
            795                 800                 805 gcc gat ggc ggc acg gtg atc ctg cag acc gac gtg acc gac ctc atc     2850
Ala Asp Gly Gly Thr Val Ile Leu Gln Thr Asp Val Thr Asp Leu Ile
    810                 815                 820 cgc atc gag cgg ctc gag cgc ggc aag atg ctc gac gat cag gcc cgc     2898
Arg Ile Glu Arg Leu Glu Arg Gly Lys Met Leu Asp Asp Gln Ala Arg
825                 830                 835 gtg atc cgc gcg acg ctc gat cac atc aat cag ggg gtc tgc atc ttc     2946
Val Ile Arg Ala Thr Leu Asp His Ile Asn Gln Gly Val Cys Ile Phe
840                 845                 850                 855 gat gcc gag ggg cgg ctc gtc ggc tgg aac cag cgc ctc ggc tcg ctg     2994
Asp Ala Glu Gly Arg Leu Val Gly Trp Asn Gln Arg Leu Gly Ser Leu
                860                 865                 870 ctc gcg atc ccg atg aac cgc ttc cgg ctg ggg gtg agc ttc ggc tac     3042
Leu Ala Ile Pro Met Asn Arg Phe Arg Leu Gly Val Ser Phe Gly Tyr
            875                 880                 885 ctg ctc gaa cgg ttc gcg cac gag atc agc ttc ggc gag ggc atg gat     3090
Leu Leu Glu Arg Phe Ala His Glu Ile Ser Phe Gly Glu Gly Met Asp
        890                 895                 900 gcg gcc cat ctc gag gcc tgg gtc cag gcg cgc cac gaa cgc gcg ccg     3138
Ala Ala His Leu Glu Ala Trp Val Gln Ala Arg His Glu Arg Ala Pro
    905                 910                 915 ctc tct ttc gag ctc cgc cgc cac gac gag ctg atc ctc gat gtc ttc     3186
Leu Ser Phe Glu Leu Arg Arg His Asp Glu Leu Ile Leu Asp Val Phe
920                 925                 930                 935 gcg cag gag atg ccc gac cgc ggc ttc gtg atg agt ttc acc gac gtc     3234
Ala Gln Glu Met Pro Asp Arg Gly Phe Val Met Ser Phe Thr Asp Val
                940                 945                 950 acc gcc gag cgg gcc gcc atc gaa gcg ctg agc cgt gcg aac gaa acg     3282
Thr Ala Glu Arg Ala Ala Ile Glu Ala Leu Ser Arg Ala Asn Glu Thr
            955                 960                 965 ctc gag gcg cgg gtg atg gag cgg acg ctg gag ctc gag gat gcg ctg     3330
Leu Glu Ala Arg Val Met Glu Arg Thr Leu Glu Leu Glu Asp Ala Leu
        970                 975                 980 ggt cat gcc gag cgg gcc aat gcc tcg cgc tcg cgc ttc gtg gcg gcg     3378
Gly His Ala Glu Arg Ala Asn Ala Ser Arg Ser Arg Phe Val Ala Ala
    985                 990                 995 gcg agc cac gat ctg ttg cag ccg ctg tcg gcg gcc aag ctc ttc atc     3426
Ala Ser His Asp Leu Leu Gln Pro Leu Ser Ala Ala Lys Leu Phe Ile
1000                1005                1010                1015 gcc acc atc ggc gac gag gcg gtg gcg ccc gaa agc cgc gag gcg ctg     3474
Ala Thr Ile Gly Asp Glu Ala Val Ala Pro Glu Ser Arg Glu Ala Leu
                1020                1025                1030 acc aag gcg cag aag gcg ctc gac tcg gtg gag ggg atc ctc ggc gcg     3522
Thr Lys Ala Gln Lys Ala Leu Asp Ser Val Glu Gly Ile Leu Gly Ala
            1035                1040                1045 ctt ctc gac atc tcg aaa ctc gag tcg ggc cgg gcg gcg gtc tcg atc     3570
Leu Leu Asp Ile Ser Lys Leu Glu Ser Gly Arg Ala Ala Val Ser Ile
        1050                1055                1060 cag ccg gtg cgc ctc gac cgg ctg atg gag gag ctc tcc gac gaa ttc     3618
Gln Pro Val Arg Leu Asp Arg Leu Met Glu Glu Leu Ser Asp Glu Phe
    1065                1070                1075 gcg ccc atc gcc gcg gcg cgc ggc ctc cgg ctc acg gtg ctg ccc tcg     3666
Ala Pro Ile Ala Ala Ala Arg Gly Leu Arg Leu Thr Val Leu Pro Ser
1080                1085                1090                1095 agc gcg gtg gtg gcc tcc gac ccg acc tat ctc cgg cgg atc ctc cag     3714
Ser Ala Val Val Ala Ser Asp Pro Thr Tyr Leu Arg Arg Ile Leu Gln
                1100                1105                1110
```

```
aac ctg atc ggc aat gcg atc cgc tac acc gcg aag ggc agg gtg ctt    3762
Asn Leu Ile Gly Asn Ala Ile Arg Tyr Thr Ala Lys Gly Arg Val Leu
            1115                1120                1125 gtc ggc gcg cgg atg acc gcg ggc atg gtg cgg ctg gag gtc tgg gac    3810
Val Gly Ala Arg Met Thr Ala Gly Met Val Arg Leu Glu Val Trp Asp
        1130                1135                1140 acc ggg ccg ggg atc gcc gag gca gat cag gag gcc atc ttc aag gag    3858
Thr Gly Pro Gly Ile Ala Glu Ala Asp Gln Glu Ala Ile Phe Lys Glu
    1145                1150                1155 ttc cac cgg ctc gac gcg ccc gcc tca ccc gcc gag ggc atg ggg ctg    3906
Phe His Arg Leu Asp Ala Pro Ala Ser Pro Ala Glu Gly Met Gly Leu
1160                1165                1170                1175 ggc ctc gcc atc gtc gag cgc gcc tgc ggg ctt ctg ggc cat ccg ctg    3954
Gly Leu Ala Ile Val Glu Arg Ala Cys Gly Leu Leu Gly His Pro Leu
                1180                1185                1190 ggg ctc cga tcc gag atc ggg cgg ggc acc tgc ttc atg ctg cag gtg    4002
Gly Leu Arg Ser Glu Ile Gly Arg Gly Thr Cys Phe Met Leu Gln Val
            1195                1200                1205 ccc cgc gcc gaa agt gcg ccc gct ccg tcc gtg ccc gat gcc tcg gcg    4050
Pro Arg Ala Glu Ser Ala Pro Ala Pro Ser Val Pro Asp Ala Ser Ala
        1210                1215                1220 gtg cgg gcg cag gcc aag gtg gcg gtg cag gac aag atc gcc ttc ctc    4098
Val Arg Ala Gln Ala Lys Val Ala Val Gln Asp Lys Ile Ala Phe Leu
    1225                1230                1235 gtc gag aat gac gac gac ctg cgt cag gcg atg gga ctg ctg ctg gag    4146
Val Glu Asn Asp Asp Asp Leu Arg Gln Ala Met Gly Leu Leu Leu Glu
1240                1245                1250                1255 aaa tgg ggg gtg agc gtg ctc gac gcg ccc tcg ggc gag gag gcg ctg    4194
Lys Trp Gly Val Ser Val Leu Asp Ala Pro Ser Gly Glu Glu Ala Leu
                1260                1265                1270 gcg ctg atc gag gag atc ggg atc ctg ccg gac ttc ttc ctc gtg gac    4242
Ala Leu Ile Glu Glu Ile Gly Ile Leu Pro Asp Phe Phe Leu Val Asp
            1275                1280                1285 cag cag ctc ggc gcg ggc atg acg ggg gtg gag ttc atc cgc acg atg    4290
Gln Gln Leu Gly Ala Gly Met Thr Gly Val Glu Phe Ile Arg Thr Met
        1290                1295                1300 cgc gac cgg cac ggg ccg gtg ccc gcc tgc atc gtg acc gcc gcc cgc    4338
Arg Asp Arg His Gly Pro Val Pro Ala Cys Ile Val Thr Ala Ala Arg
    1305                1310                1315 cgc ccc gaa gtg gcc gcc ctc tgc gcc gag acg ggc atc cgg ctg atc    4386
Arg Pro Glu Val Ala Ala Leu Cys Ala Glu Thr Gly Ile Arg Leu Ile
1320                1325                1330                1335 cag aaa ccc atc gac gcc cgc gtg ctc gag gag ttc ctg cgc gcc ctc    4434
Gln Lys Pro Ile Asp Ala Arg Val Leu Glu Glu Phe Leu Arg Ala Leu
                1340                1345                1350 tag ggctgccgga cggcagcggc ggcgcgtcaa aggcatccct cgcccggtca         4487
gtcccgcgtc actacgacca aggtcacata gccgcagcgt caggtttggt cctactctcg  4547
gcgcaataag gggggatctg ccatgctgct agccgatcag agaaccattg ccgccgaccc  4607
tgcgacggtc tgggcggcca tcctcgaccc cgaggtgctg aggtctgca ttcccggatg   4667 cgagagcctg acgggcagcc cctccgaggg ctacgaggcg atcgtgaccc agaaggtggg  4727
tcccgtgaag gcgcgcttca ccggccatgt cacgctgtcg acatcgtgg aggggcagtc   4787 gctcaccatc tcgggtgaag gcaagggcgg ggccgcggg                        4826

<210> SEQ ID NO 4
<211> LENGTH: 226
```

```
<212> TYPE: PRT
<213> ORGANISM: Rhodobacter sphaeroides

<400> SEQUENCE: 4

Met Ile Glu Pro Ser Arg Pro Leu Gln Ser Ala Leu Ile Val Asp Asp
 1               5                  10                  15

His Pro Leu Phe Cys Asp Ala Leu Ser Met Thr Leu Lys Ala Val Ala
            20                  25                  30

Gly Leu Thr His Ile Glu Ser Ala Asp Arg Leu Glu Thr Ala Leu Ala
        35                  40                  45

Arg Leu Asp Leu Gln Pro Ala Phe Asp Val Val Leu Asp Leu Asn
 50                  55                  60

Leu Pro Asp Val Asn Gly Leu Asp Gly Leu Ile Arg Leu Lys Ala Ser
 65                  70                  75                  80

Leu Gly Ala Val Pro Val Val Val Ser Leu Ala Asp Asn Arg
                85                  90                  95

Val Ile Gly Ala Ala Leu Lys Ala Gly Ala Ala Gly Phe Val Pro Lys
                100                 105                 110

His Ser Arg Arg Glu Val Phe Arg Ala Ala Phe Asp Ala Ile Arg Glu
            115                 120                 125

Gly Arg Ser Tyr Leu Pro Glu Gly Phe Thr Pro His Ser Pro Gly Ala
130                 135                 140

Pro Ala Ser Gln Arg Glu Glu Ala Ile Ala Arg Leu Ala Leu Leu Thr
145                 150                 155                 160

Arg Gln Gln Ala Lys Ile Leu Gln Leu Ile Cys Glu Gly Arg Leu Asn
                165                 170                 175

Lys Gln Ile Ala Tyr Asp Leu Thr Ile Ala Glu Thr Thr Val Lys Ala
            180                 185                 190

His Val Thr Ala Ile Met Arg Lys Leu Gly Val Gln Ser Arg Thr Gln
        195                 200                 205

Ala Val Leu Met Val Gln Glu Ala Ser Phe Ala Ser Leu Met Pro Glu
    210                 215                 220

Asn Ser
225

<210> SEQ ID NO 5
<211> LENGTH: 390
<212> TYPE: PRT
<213> ORGANISM: Rhodobacter sphaeroides

<400> SEQUENCE: 5

Met Glu Gly Leu Arg Glu Arg Ala Val Ala Ala Glu Arg Asn Gly Ala
 1               5                  10                  15

Pro Leu Val Arg Ser Ala His Leu Pro Gly Asp Val Pro Ala Ala Ala
            20                  25                  30

Glu Arg Leu Ala Glu Ala Leu Gly Glu Gly Pro Phe Ala Leu Val Ile
        35                  40                  45

Leu Phe Val Thr Pro Glu Thr Asp Val Ser Ala Leu Ala Leu Gly Ala
    50                  55                  60

Gln Glu Val Phe Gly Pro Val Pro Val Ile Gly Cys Thr Thr Ala Gly
 65                  70                  75                  80

Glu Ile Ser Ala Glu Gly Tyr Thr Glu Gly Glu Val Val Ala Val Ala
                85                  90                  95

Leu Pro Ala Ala His Phe His Val Arg Pro Ile Leu Ile Gly Ala Leu
                100                 105                 110
```

```
Ala Asp Leu Asp Arg Glu Glu Leu Ile Gly Arg Leu Ile Arg Glu Arg
            115                 120                 125

Asp Ala Leu Ala Arg Glu Arg Pro Asp Trp Gly Ser Glu Phe Ala Phe
        130                 135                 140

Leu Met Val Asp Gly Leu Ser Thr Arg Glu Asp Glu Leu Ala Ser Thr
145                 150                 155                 160

Leu Ala Ala Gly Leu Gly Pro Val Pro Leu Phe Gly Gly Ser Ala Ala
                165                 170                 175

Asp Gly Val Arg Phe Arg Glu Thr Phe Val Ile His Gly Ala Asp Val
            180                 185                 190

Leu Arg Asp Ala Ala Val Leu Ala Leu Val Arg Ser Asp Cys Arg Val
        195                 200                 205

Arg Val Phe Asn Leu Asp His Phe Arg Pro Thr Asp Gln Arg Met Val
    210                 215                 220

Val Thr Glu Ala Asp Pro Ala Arg Arg Ile Val Arg Arg Ile Asn Ala
225                 230                 235                 240

Glu Pro Ala Ala Gln Glu Tyr Ala Arg Leu Leu Gly Lys Asp Pro Gly
                245                 250                 255

Gln Leu Asp Ser Phe Thr Phe Ala Ala His Pro Val Val Arg Ile
            260                 265                 270

Gly Gly Lys His His Val Arg Ala Ile Arg Glu Val Ala Pro Asn Ala
        275                 280                 285

Ile Ser Phe Phe Phe Ser Ala Ile Asp Glu Gly Leu Val Leu Ala Leu
    290                 295                 300

Ala Glu Pro Gln Asp Leu Val Gly His Leu Thr Asp Glu Leu Ala Gly
305                 310                 315                 320

Leu Gly Arg Glu Arg Glu Pro Ser Ala Ile Val Ala Cys Asp Cys Val
                325                 330                 335

Leu Arg Arg Met Glu Ala Leu Asp Ser Gln Ser Ile Gly Ala Val Ser
            340                 345                 350

Ala Leu Leu Arg Arg His Arg Val Val Gly Phe Ser Thr Tyr Gly Glu
        355                 360                 365

Gln Leu Asn Gly Met His Val Asn Gln Thr Met Thr Gly Val Ala Ile
    370                 375                 380

Tyr Pro Pro Glu Glu Arg
385                 390

<210> SEQ ID NO 6
<211> LENGTH: 733
<212> TYPE: PRT
<213> ORGANISM: Rhodobacter sphaeroides

<400> SEQUENCE: 6

Met Ser Leu Ala Leu Ile Asp Pro Ser Asp Pro Pro Glu Arg Gln Arg
1               5                   10                  15

Asp Lys Leu Leu Glu Ile Val Arg Ala Leu Met Ala Arg Val Glu Arg
            20                  25                  30

Thr Thr Asp Asp Gly Gly Ala Ala Tyr Ala Gln Phe Gln Arg Ala Ala
        35                  40                  45

Met Leu Glu Asp Gln Val Arg Glu Arg Thr Ala Asp Leu Gln Arg Thr
    50                  55                  60

Leu Glu Leu Leu Asn Leu Ser Asn Glu Arg Leu Ala Glu Ala Thr Arg
65                  70                  75                  80

Ala Ala Glu Glu Ala Arg Gln Asn Leu Ala Asn Ala Ile Glu Thr Val
                85                  90                  95
```

```
Gln Glu Gly Phe Ala Leu Phe Asp Ala Asp Asp Val Leu Val Leu Cys
            100                 105                 110
Asn Leu Arg Phe Gly Met His Met Leu Asp Ile Gln Glu His Leu Arg
            115                 120                 125
Pro Gly Leu Ser Phe Gly Gly Tyr Ile Asp Arg Val Ser Arg Ser Arg
            130                 135                 140
Tyr Leu Ala Leu Pro Glu Ala Glu Thr Pro Glu Asp Trp Ala Val Arg
145                 150                 155                 160
Arg Lys Arg Arg His Tyr Asp Arg His Ser Ile Phe Asn Val Arg Leu
                165                 170                 175
Ile Trp Asp Arg Trp Leu Gln Val Ser Glu His Arg Thr Ala Asp Gly
            180                 185                 190
Gly Thr Val Ile Leu Gln Thr Asp Val Thr Asp Leu Ile Arg Ile Glu
            195                 200                 205
Arg Leu Glu Arg Gly Lys Met Leu Asp Asp Gln Ala Arg Val Ile Arg
            210                 215                 220
Ala Thr Leu Asp His Ile Asn Gln Gly Val Cys Ile Phe Asp Ala Glu
225                 230                 235                 240
Gly Arg Leu Val Gly Trp Asn Gln Arg Leu Gly Ser Leu Leu Ala Ile
                245                 250                 255
Pro Met Asn Arg Phe Arg Leu Gly Val Ser Phe Gly Tyr Leu Leu Glu
            260                 265                 270
Arg Phe Ala His Glu Ile Ser Phe Gly Glu Gly Met Asp Ala Ala His
            275                 280                 285
Leu Glu Ala Trp Val Gln Ala Arg His Glu Arg Ala Pro Leu Ser Phe
            290                 295                 300
Glu Leu Arg Arg His Asp Glu Leu Ile Leu Asp Val Phe Ala Gln Glu
305                 310                 315                 320
Met Pro Asp Arg Gly Phe Val Met Ser Phe Thr Asp Val Thr Ala Glu
                325                 330                 335
Arg Ala Ala Ile Glu Ala Leu Ser Arg Ala Asn Glu Thr Leu Glu Ala
            340                 345                 350
Arg Val Met Glu Arg Thr Leu Glu Leu Glu Asp Ala Leu Gly His Ala
            355                 360                 365
Glu Arg Ala Asn Ala Ser Arg Ser Arg Phe Val Ala Ala Ala Ser His
            370                 375                 380
Asp Leu Leu Gln Pro Leu Ser Ala Ala Lys Leu Phe Ile Ala Thr Ile
385                 390                 395                 400
Gly Asp Glu Ala Val Ala Pro Glu Ser Arg Glu Ala Leu Thr Lys Ala
                405                 410                 415
Gln Lys Ala Leu Asp Ser Val Glu Gly Ile Leu Gly Ala Leu Leu Asp
            420                 425                 430
Ile Ser Lys Leu Glu Ser Gly Arg Ala Ala Val Ser Ile Gln Pro Val
            435                 440                 445
Arg Leu Asp Arg Leu Met Glu Glu Leu Ser Asp Glu Phe Ala Pro Ile
            450                 455                 460
Ala Ala Ala Arg Gly Leu Arg Leu Thr Val Leu Pro Ser Ser Ala Val
465                 470                 475                 480
Val Ala Ser Asp Pro Thr Tyr Leu Arg Arg Ile Leu Gln Asn Leu Ile
                485                 490                 495
Gly Asn Ala Ile Arg Tyr Thr Ala Lys Gly Arg Val Leu Val Gly Ala
            500                 505                 510
```

```
Arg Met Thr Ala Gly Met Val Arg Leu Glu Val Trp Asp Thr Gly Pro
        515                 520                 525

Gly Ile Ala Glu Ala Asp Gln Glu Ala Ile Phe Lys Glu Phe His Arg
        530                 535                 540

Leu Asp Ala Pro Ala Ser Pro Ala Glu Gly Met Gly Leu Gly Leu Ala
545                 550                 555                 560

Ile Val Glu Arg Ala Cys Gly Leu Leu Gly His Pro Leu Gly Leu Arg
                565                 570                 575

Ser Glu Ile Gly Arg Gly Thr Cys Phe Met Leu Gln Val Pro Arg Ala
                580                 585                 590

Glu Ser Ala Pro Ala Pro Ser Val Pro Asp Ala Ser Ala Val Arg Ala
        595                 600                 605

Gln Ala Lys Val Ala Val Gln Asp Lys Ile Ala Phe Leu Val Glu Asn
        610                 615                 620

Asp Asp Asp Leu Arg Gln Ala Met Gly Leu Leu Leu Glu Lys Trp Gly
625                 630                 635                 640

Val Ser Val Leu Asp Ala Pro Ser Gly Glu Glu Ala Leu Ala Leu Ile
                645                 650                 655

Glu Glu Ile Gly Ile Leu Pro Asp Phe Phe Leu Val Asp Gln Gln Leu
                660                 665                 670

Gly Ala Gly Met Thr Gly Val Glu Phe Ile Arg Thr Met Arg Asp Arg
                675                 680                 685

His Gly Pro Val Pro Ala Cys Ile Val Thr Ala Ala Arg Arg Pro Glu
        690                 695                 700

Val Ala Ala Leu Cys Ala Glu Thr Gly Ile Arg Leu Ile Gln Lys Pro
705                 710                 715                 720

Ile Asp Ala Arg Val Leu Glu Glu Phe Leu Arg Ala Leu
                725                 730

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
attgacctcc atgatctcga                                          20
```